US012582629B1

(12) United States Patent
Le Roux et al.

(10) Patent No.: US 12,582,629 B1
(45) Date of Patent: Mar. 24, 2026

(54) EXTENDED-RELEASE PHARMACEUTICAL COMPOSITIONS OF RALINEPAG

(71) Applicants: Danielle Marie Le Roux, West Milford, NJ (US); Jayendrakumar Dasharathlal Patel, Robbinsville, NJ (US)

(72) Inventors: Danielle Marie Le Roux, West Milford, NJ (US); Jayendrakumar Dasharathlal Patel, Robbinsville, NJ (US)

(73) Assignee: Innovate Therapeutics LLC, Princeton, NJ (US)

( * ) Notice: Subject to any disclaimer, the term of this patent is extended or adjusted under 35 U.S.C. 154(b) by 0 days.

(21) Appl. No.: 19/367,677

(22) Filed: Oct. 23, 2025

(51) Int. Cl.
| | |
|---|---|
| *A61K 9/00* | (2006.01) |
| *A61K 9/20* | (2006.01) |
| *A61K 9/50* | (2006.01) |
| *A61K 31/325* | (2006.01) |

(52) U.S. Cl.
CPC .......... *A61K 31/325* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/205* (2013.01); *A61K 9/2054* (2013.01); *A61K 9/2086* (2013.01); *A61K 9/2095* (2013.01); *A61K 9/501* (2013.01); *A61K 9/5015* (2013.01); *A61K 9/5036* (2013.01); *A61K 9/5042* (2013.01); *A61K 9/5089* (2013.01)

(58) Field of Classification Search
None
See application file for complete search history.

(56) References Cited

FOREIGN PATENT DOCUMENTS

| | | | | |
|---|---|---|---|---|
| CA | 2777856 A1 * | 4/2011 | ........... | A61K 9/2027 |
| WO | WO-2018089804 A9 * | 6/2018 | ............. | A61P 43/00 |

* cited by examiner

*Primary Examiner* — Susan T Tran

(57) ABSTRACT

The present invention relates to extended-release pharmaceutical compositions comprising Ralinepag or a pharmaceutically acceptable salt, solvate, or prodrug thereof, formulated for low-dose oral administration to provide controlled release of the active ingredient over about 8 to 24 hours. The compositions comprise Ralinepag in an amount from about 0.03 mg to about 1.2 mg per unit dose, together with one or more pharmaceutically acceptable carriers, at least one of which functions as a release rate-controlling polymer. The invention employs integrated, process-critical manufacturing methods—including geometric dilution, geometric sifting and blending, solution-spray or melt granulation, dry granulation, and continuous direct compression—to achieve uniform drug distribution and superior content uniformity at ultra-low dose levels, meeting or exceeding USP <905> criteria. The resulting formulations exhibit alcohol-resistant extended-release performance under conditions up to 40% v/v ethanol and may be configured as matrix, reservoir, or osmotic systems, optionally with pH-sensitive or alcohol-resistant coatings, thereby ensuring reproducible pharmacokinetic performance, reduced $C_{max}$-related side effects, and improved patient compliance.

18 Claims, No Drawings

EXTENDED-RELEASE PHARMACEUTICAL COMPOSITIONS OF RALINEPAG

FIELD OF THE INVENTION

The present invention relates to pharmaceutical compositions and manufacturing methods for extended-release (ER) oral dosage forms of Ralinepag or its pharmaceutically acceptable salts, solvates, or prodrugs. More particularly, the invention pertains to low-dose, alcohol-resistant, controlled-release formulations of Ralinepag that provide sustained plasma exposure, reduced $C_{max}$-related adverse effects, and improved therapeutic tolerability for the treatment of pulmonary arterial hypertension (PAH) and related prostacyclin-responsive disorders. The invention further encompasses critical process parameters and compositional designs enabling enhanced content uniformity (CU) and release robustness under both aqueous and hydroalcoholic conditions. The present invention also relates method of treatment using the presently disclosed pharmaceutical composition.

BACKGROUND OF THE INVENTION

Ralinepag is a potent, selective prostacyclin (IP) receptor agonist characterized by high receptor affinity and an elimination half-life of approximately 19-26 hours. Immediate-release formulations of Ralinepag achieve rapid absorption with a $T_{max}$ of about 1.0-1.5 hours, often leading to elevated peak plasma concentrations ($C_{max}$) and intolerable prostacyclin-related side effects such as headache, flushing, and hypotension. Clinical data demonstrate that immediate-release forms are tolerated up to approximately 100 μg, whereas higher doses (e.g., 200 μg) frequently cause adverse events necessitating treatment discontinuation. These limitations highlight the need for extended-release systems capable of mitigating $C_{max}$-driven side effects while maintaining therapeutic exposure (AUC).

Extended-release (ER) formulations offer pharmacokinetic advantages by modulating absorption and prolonging drug release, but conventional ER systems often exhibit instability in the presence of alcohol, leading to premature drug release ("dose dumping"). Ethanol can alter polymer hydration and matrix integrity, compromising release control and causing excessive drug release, thereby increasing systemic exposure and the risk of adverse reactions.

Furthermore, Ralinepag is typically administered in ultra-low doses (0.3-1.4 mg per unit), posing significant content uniformity challenges during formulation and scale-up. At such low loadings, segregation, particle-size variability, and blending inefficiencies can result in unacceptable variability, particularly in direct-compression or granulation processes. The need therefore exists for robust manufacturing methods and optimized excipient systems that ensure uniform Ralinepag distribution, consistent dissolution, and alcohol-resistant release across dosage forms and strengths.

Accordingly, there remains a need for an extended-release formulation platform that ensures consistent, safe, and reproducible pharmacokinetic performance, independent of ethanol co-ingestion, while enabling multi-strength scalability and manufacturing robustness.

SUMMARY OF THE INVENTION

The present invention provides extended-release (ER) pharmaceutical compositions of Ralinepag, or its pharmaceutically acceptable salts, solvates, or prodrugs, that deliver the active ingredient at a controlled and sustained rate over a period of about 8 to 24 hours, preferably 8 to 20 hours, following oral administration.

Ralinepag is a potent and selective prostacyclin (IP) receptor agonist characterized by high receptor affinity and a prolonged elimination half-life (approximately 19-26 hours). While immediate-release (IR) formulations of Ralinepag achieve rapid absorption, they produce high peak plasma concentrations ($C_{max}$) that often lead to intolerable prostacyclin-related adverse events, such as headache, flushing, and hypotension. The extended-release compositions disclosed herein mitigate these issues by modulating the rate of absorption, thereby reducing $C_{max}$-related side effects while maintaining the desired systemic exposure (AUC) and improving patient compliance through once- or twice-daily dosing.

The inventive compositions are configured to be alcohol-resistant, maintaining their release kinetics and matrix integrity in the presence of ethanol-containing beverages up to 40% (v/v). In preferred embodiments, the compositions provide a 12-hour peak-to-trough plasma concentration ratio of less than about 4, preferably less than 3.5, and more preferably less than 2.5, under both alcoholic and non-alcoholic conditions. When tested in 900 mL of 40% ethanolic aqueous media using USP Apparatus II (paddle method, 50-100 rpm, 37±1° C.), the formulations release less than about 75%, such as less than 60%, 50%, 40%, of Ralinepag at 2 hours, demonstrating robust alcohol resistance extended-release performance.

The present invention also provides novel manufacturing methods and integrated process controls specifically optimized for low-dose Ralinepag formulations (for example, about 0.3 mg to about 1.8 mg per unit, preferably less than 1.4 mg). These processes—including solution-spray granulation, fluid-bed granulation, geometric dilution, geometric sifting and blending, melt granulation, roller compaction, and continuous direct compression—ensure reproducible content uniformity (CU) within the limits specified by USP <905>. The coordinated design of excipient selection and process sequence minimizes segregation and variability, achieving uniform dispersion of Ralinepag at the micron level within single-unit and multi-unit dosage systems.

In certain embodiments, the invention provides multiple formulation architectures selected from five principal classes of extended-release systems: (i) Matrix-based systems, in which Ralinepag is embedded in a hydrophilic, hydrophobic, or amphiphilic polymer matrix that controls release by diffusion or erosion; (ii) Membrane-moderated (reservoir) systems, wherein Ralinepag resides in a coated core surrounded by a controlled-permeability polymeric membrane; (iii) Osmotic-controlled systems, wherein drug release is driven by osmotic pressure through a semipermeable membrane containing precision-drilled orifices; (iv) pH-sensitive (enteric) delayed-release systems, which restrict release in the stomach and initiate release at intestinal pH; and (v) bi-phasic or multi-phasic systems, which incorporate a rapid-onset immediate-release layer or coating for early therapeutic effect followed by sustained release from a core or secondary layer. Each system is configured to maintain alcohol resistance, low-dose uniformity, and predictable release kinetics across manufacturing scales.

In a further aspect, the invention provides a controlled-scaling strategy for fabricating two or more dosage strengths of Ralinepag extended-release compositions. Unlike conventional weight-proportional scaling, which alters geometric and diffusive parameters and leads to variable ethanol sensitivity, the present invention restricts inter-strength deviation in total tablet or unit weight to no more than about 50%, such as not more than 40%, 30%, 20%, or 10%, and limits the variation in the absolute amount (in milligrams) of release-controlling polymers between strengths to similar bounds. This ensures that the matrix density, polymer-to-drug ratio, and surface-area-to-volume relationship remain substantially consistent among strengths, thereby preserving dissolution kinetics, alcohol resistance, and pharmacokinetic reproducibility across the entire dose range.

Collectively, the present invention establishes an integrated formulation and process approach for the development of low-dose, alcohol-resistant, extended-release Ralinepag compositions. By harmonizing excipient functionality, process parameters, and scaling controls, the invention provides compositions that exhibit excellent content uniformity, robust alcohol-insensitive extended-release, and consistent therapeutic performance across multiple strengths, offering a significant advancement over conventional extended-release and matrix technologies.

DETAILED DESCRIPTION OF THE INVENTION

The terms used in this specification generally have their ordinary and customary meanings in the art, within the context of this invention and in the specific context where each term is used. Certain terms are further defined below, or elsewhere in the specification, to provide additional clarity to practitioners in describing the compositions and methods of the invention and in understanding how to make and use them.

As used herein, the use of the article "a" or "an" in conjunction with the term "comprising" in the claims and/or specification can mean "one," but is also consistent with the meaning of "one or more," "at least one," and "one or more than one." Furthermore, the terms "having," "including," "containing," "comprising," "consisting essentially of" and "comprises" are interchangeable and shall be understood as open-ended terms, permitting the inclusion of additional, unrecited elements, features, or steps.

The term "about" or "approximately" as used herein refers to a value within an acceptable error range for a given parameter as would be recognized by one of ordinary skill in the art. By way of example, "about" may indicate a variation of up to ±25%, ±15%, ±10%, ±5%, or ±1% from the stated value, unless otherwise indicated or apparent from the context.

In the context of the present invention, the term "side effects", "adverse event", "adverse effect" and similar type of words refers to physiological effects on one or more systems of the body—such as the cardiovascular, nervous, or gastrointestinal systems—that may cause discomfort or adverse symptoms in the subject and that are directly or indirectly attributable to the administration of Ralinepag or its pharmaceutically acceptable salts, solvates, or prodrugs. Non-limiting examples include headache, flushing, hypotension, or gastrointestinal discomfort.

As used herein, the terms "drug," "active," "active ingredient," or "drug substance" refer to Ralinepag or its pharmaceutically acceptable salts, solvates, polymorphs, hydrates, co-crystals, or prodrugs, as applicable.

The terms "administration" or "ingestion", as used herein, refer to the act of introducing the pharmaceutical dosage form into the body, typically by oral swallowing, unless otherwise indicated.

The present invention is not limited to any particular chemical or physical form of Ralinepag or its pharmaceutically acceptable derivatives. The active substance may be employed in any suitable form, including but not limited to the base form, pharmaceutically acceptable salts, hydrates, anhydrous forms, solvates, polymorphic forms, amorphous or crystalline forms, co-crystals, clathrates, or single- or multi-component crystal forms. All such forms of Ralinepag or its equivalents are considered within the scope of the present invention.

The pharmaceutical compositions that constitute the subject matter of the present invention are controlled-release formulations of Ralinepag or its pharmaceutically acceptable salts, solvates, or prodrugs. The compositions are suitable for administration to mammals, including humans, preferably via a non-parenteral route, most preferably the oral route.

As used herein, the term "controlled release" or "extended release" is intended to be generic and inclusive of "sustained release," "pulsatile release," "ascending release," and "delayed release" profiles. Controlled release systems are designed to deliver the active agent at a predetermined rate and/or to a specific region of the gastrointestinal tract, thereby maintaining therapeutic plasma concentrations over an extended duration.

For the purpose of this disclosure, various embodiments of controlled- or extended-release dosage forms of Ralinepag have been described herein as "sustained-release" or "controlled-release" embodiments for simplicity. Without limitation, such dosage forms may: (i) release Ralinepag gradually and continuously over a predetermined period; (ii) exhibit a monophasic, biphasic or pulsatile release, wherein small amount (<about 35% w/w as immediate release dose of total amount of drug present in the formulation) in immediate release or no drug is released for an initial period followed by a rapid, sustained, or delayed release phase; or (iii) release small amount (<about 35% w/w as immediate release dose of total amount of drug present in the formulation) in immediate release or no Ralinepag in the stomach while enabling rapid or sustained release in the intestinal environment.

It will be appreciated by those skilled in the art that certain sustained-release embodiments may also be classified as delayed-release or pulsatile-release systems, and vice versa. For example, an osmotic pump formulation may exhibit an initial lag phase during which osmotic pressure builds within the device, resulting in minimal drug release before steady-state diffusion begins. Such dosage forms may therefore be regarded as both sustained-release and pulsatile-release systems within the scope of the present invention.

More specifically, the term "controlled" or "extended-release" (ER) refers to a dosage form or pharmaceutical composition that releases Ralinepag or its pharmaceutically acceptable salts, solvates, or prodrugs over an extended period of time, thereby maintaining therapeutically effective plasma concentrations for a prolonged duration following administration. The release profile may be governed by diffusion, erosion, osmotic pressure, swelling, pH-dependent solubility, or a combination thereof. In one embodiment, the extended-release system provides controlled release of Ralinepag for at least about 6 hours, preferably 8 to 24 hours, and more preferably 12 to 24 hours, thereby enabling once- or twice-daily administration. The term "extended-release" as used herein is intended to encompass matrix-type, reservoir-type, osmotic-controlled, pH-sensitive, and multiparticulate systems, as well as combinations thereof, unless otherwise specified.

As used herein, the term "alcohol-resistant" or "alcohol-insensitive" dosage form refers to an extended-release composition of Ralinepag that maintains its designed release rate and does not exhibit dose dumping or premature release when exposed to hydroalcoholic environments representative of gastrointestinal co-ingestion of ethanol. In certain embodiments, the formulation maintains its release characteristics in the presence of aqueous media containing up to 40% v/v ethanol, preferably 20-40% v/v, without significant deviation (for example, not more than ±about 35%, such as ±about 30, ±about 25, ±about 20) from the relative dissolution rate observed in corresponding aqueous media. Also, the term "alcohol-resistant" or "alcohol-insensitive" dosage form also refers to an extended-release composition of Ralinepag that release not more than 75% w/w, such as not more than 60%, 50%, 40% w/w, of the drug contained in the composition at 2 hours in the presence of aqueous media containing up to 40% v/v ethanol, preferably 20-40% v/v. Such resistance is achieved through the judicious selection of controlled-release polymers, lipids, and excipients.

The term "content uniformity (CU)", as used herein, refers to the uniform distribution of Ralinepag or its pharmaceutically acceptable salts, solvates, or prodrugs within a dosage form, such that each individual unit contains an amount of the active ingredient within acceptable limits as defined by United States Pharmacopeia (USP)<905> Content Uniformity or equivalent pharmacopeial standards. In the context of the present invention, maintaining CU is of particular importance given the ultra-low drug loading (e.g., about 0.3 mg to about 1.4 mg per unit) typical of the Ralinepag extended-release formulations. The inventive processes disclosed herein are specifically designed to achieve low relative standard deviation (RSD) and to ensure CU values within 85-115% of label claim, with an acceptance value (AV)≤15.

As used herein, the term "low-dose" refers to a pharmaceutical dosage form in which the quantity of Ralinepag or its pharmaceutically acceptable salts, solvates, or prodrugs per individual unit is sufficiently small that achieving homogenous distribution of the active ingredient throughout the formulation presents a significant manufacturing challenge. In one embodiment, the term encompasses formulations containing less than about 5% w/w, preferably less than about 2% w/w, and more preferably less than about 1% w/w of Ralinepag relative to the total composition weight. In another embodiment, low-dose formulations of the present invention may contain about 0.03 mg to about 3.0 mg, such as <2.5 mg, <2 mg, <1.5 mg, <1.4 mg of Ralinepag per unit dose, depending on therapeutic requirements. Such low-dose systems are particularly susceptible to content variability, segregation, and demixing, especially when processed through conventional blending or compression methods. The inventive manufacturing strategies disclosed herein— such as solution-spray granulation, geometric dilution, geometric sifting, and continuous direct compression—have been specifically developed to ensure uniformity of low-dose Ralinepag across unit operations and dosage units.

As used herein, the term "segregation control" refers to the collective set of formulation and process design strategies employed to minimize or prevent the non-uniform spatial distribution of Ralinepag or its pharmaceutically acceptable salts, solvates, or prodrugs within a powder blend, granulation, or final dosage form. Segregation may arise from differences in particle size, density, shape, surface energy, or flowability between the active ingredient and excipients, leading to variability in content uniformity and drug release.

Ralinepag is a potent and selective prostacyclin (IP) receptor agonist exhibiting high receptor affinity. Immediate release ralinepag formulation provide a prolonged elimination half-life of approximately 19 to 26 hours, the characteristics that render it well suited for once-daily administration in the treatment of pulmonary arterial hypertension (PAH). The maximum plasma concentration ($C_{max}$) of immediate-release Ralinepag typically occurs within approximately 1.0 to 1.5 hours post-dose. Despite the prolonged half-life of the immediate-release (IR) formulations of Ralinepag, its rapid absorption and elevated peak plasma concentrations ($C_{max}$) produces intolerable dose-limiting prostacyclin-related adverse effects. Clinical observations demonstrate that, in single ascending dose studies, Ralinepag in immediate-release form is tolerated at doses up to approximately 100 μg, whereas higher doses such as 200 μg result in intolerable adverse events leading to treatment discontinuation, reflecting a rapid absorption profile that contributes to $C_{max}$-related side effects.

The present invention provides an extended-release (ER) pharmaceutical composition of ralinepag or its pharmaceutically acceptable salts, solvates, or prodrugs (such as disclosed in PCT/US2023/015518, which is incorporated herein in its entirety) that substantially prolonged the rate of absorption and flattens the plasma concentration-time profile of the drug, thereby improving clinical tolerability through reduction of $C_{max}$-related adverse events while maintaining the overall systemic exposure (AUC) required for therapeutic efficacy. By controlling the rate of drug release and absorption, the extended-release formulation provides reduced pharmacokinetic variability and improved patient adherence compared with an equivalent once-daily immediate-release formulation of Ralinepag.

In a further embodiment, the ingestion of the extended-release (ER) pharmaceutical composition of ralinepag or its pharmaceutically acceptable salts, solvates, or prodrugs (such as disclosed in PCT/US2023/015518, which is incorporated herein in its entirety) with alcoholic beverages containing up to about 40% alcohol by volume may compromise release control if release rate controlling excipient (s) of the composition are not properly selected. Alcohol can alter the integrity of release rate controlling polymeric matrices or coatings by accelerating polymer hydration, swelling, or dissolution, potentially resulting in unintended rapid release of the ralinepag or its pharmaceutically acceptable salts, solvates, or prodrugs, a phenomenon commonly referred to as "dose dumping." Such rapid release may cause undesirably high plasma concentrations and an increased risk of adverse prostacyclin-related effects. Therefore, the selection and optimization of release rate-controlling ingredients and their concentration within the extended-release composition of ralinepag or its pharmaceutically acceptable salts, solvates, or prodrugs are critical to maintaining formulation integrity under alcoholic conditions.

Accordingly, the present invention provides extended-release compositions of ralinepag or its pharmaceutically acceptable salts, solvates, or prodrugs that retain their controlled-release performance when administered with alcoholic beverages (containing up to 40% alcohol). More specifically, the compositions of the invention provide a controlled and sustained pharmacokinetic profile that remains stable in the presence or absence of alcohol. Following oral administration of the presently disclosed composition, with or without an alcoholic beverage containing up to about 40% alcohol by volume, it provides 12-hour peak-to-trough plasma concentration ratio of less than about 4, preferably less than about 3.5, and more preferably less than about 2.5. The term or phrase "12-hour peak-to-trough plasma concentration ratio" refers to ratio calculated by dividing maximum plasma concentration of ralinepag (or its pharmaceutically acceptable salts, solvates, or prodrugs) with plasma concentration of ralinepag (or its pharmaceutically acceptable salts, solvates, or prodrugs, respectively) at 12 hours. In a further aspect, when the presently disclosed composition administered with alcoholic beverages containing up to about 40% alcohol by volume, it provide an 12-hour peak-to-trough plasma concentration ratio of ralinepag (or its pharmaceutically acceptable salts, solvates, or prodrugs) within about 25% to 175%, such as about 35% to 165%, about 50% to 150%, about 60% to 140%, about 75% to 125%, or about 80% to 125% relative to the corresponding values obtained under non-alcoholic conditions. These results demonstrate that the compositions effectively preserving the extended-release characteristics when administered with alcoholic beverages, thereby improving clinical tolerability through reduction of $C_{max}$-related adverse events while maintaining the overall systemic exposure (AUC) required for therapeutic efficacy.

Consequently, the present invention provides extended-release compositions of ralinepag or its pharmaceutically acceptable salts, solvates, or prodrugs that maintain controlled release and absorption kinetics of ralinepag or its pharmaceutically acceptable salts, solvates, or prodrugs, respectively, under both alcoholic and non-alcoholic conditions, thereby ensuring consistent pharmacological performance, enhanced safety, and improved clinical outcomes in the treatment of pulmonary arterial hypertension and related prostacyclin-responsive adverse events. Overall, by stabilizing drug release in both aqueous and alcoholic environments, the formulations ensure consistent bioavailability, avoid erratic spikes in systemic concentration, and thereby reduce Cmax-driven adverse effects associated with rapid absorption.

In further embodiment, the extended-release compositions described herein are formulated to deliver Ralinepag at a controlled rate that prolongs absorption and maintains plasma concentrations within the therapeutic window for a period of approximately 8 to 24 hours, such as 8 to 22 hours, 8 to 20 hours. Owing to the controlled-release mechanism and reduced absorption rate through the gastrointestinal tract, the absolute bioavailability of Ralinepag from such controlled release formulations may be moderately lower than that observed with immediate-release dosage forms. To achieve comparable systemic exposure, the total daily dose of Ralinepag administered in the extended-release formulation may therefore be about 10% to 80%, such as 15 to 65%, 30% to 50%, 10 to 50%, 15 to 30% greater than that required in the immediate-release formulation. This adjustment reflects that pharmacokinetic optimization is crucial and necessitate for the controlled-release design to attain similar exposure (AUC), while the resulting plasma profile demonstrates sustained exposure with lower $C_{max}$ and extended $T_{max}$, leading to reduced incidence of peak-related side effects while maintaining therapeutic efficacy over the extended period of time.

In further embodiments, this invention provides a controlled release pharmaceutical composition of Ralinepag or its pharmaceutically acceptable salts, solvates, or prodrugs that affords protection against alcohol dose dumping following oral administration with an alcoholic beverage (contain upto 40% alcohol), such that it provides a relative mean or median AUC and/or Cmax of the Ralinepag or its pharmaceutically acceptable salts, solvates, or prodrugs not more than 150%, such as not more than 145%, not more than 140%, not more than 135%, not more than 130% and not more than 125% relative to the mean or median AUC and/or Cmax, respectively, of the Ralinepag or its pharmaceutically acceptable salts, solvates, or prodrugs, respectively, obtained following the oral administration of the same dose of the controlled release pharmaceutical composition of Ralinepag or its pharmaceutically acceptable salts, solvates, or prodrugs with a non-alcoholic beverage.

In further embodiment, the presently disclosed controlled release pharmaceutical composition of ralinepag or its pharmaceutically acceptable salts, solvates, or prodrugs provides a mean or median Tmax greater than about 2.5 hours, specifically more than 4 hours, and more specifically more than 5 hours, such as more than 6 hours, more than 8 hours, following oral administration, regardless of the co-administration of the alcoholic beverages. In further embodiment, the presently disclosed controlled release pharmaceutical composition of ralinepag or its pharmaceutically acceptable salts, solvates, or prodrugs affords protection against alcohol dose dumping following oral administration with the alcoholic beverage, such that it provide a relative mean or median $T_{max}$ of the ralinepag or its pharmaceutically acceptable salts, solvates, or prodrugs in a range of about 25% to 200%, such as 50% to 150%, 60% to 140%, 70% to 130%, 80% to 125% of the relative mean or median $T_{max}$ of the Ralinepag or its pharmaceutically acceptable salts, solvates, or prodrugs, respectively, obtained following the oral administration of the same dose of the controlled release pharmaceutical composition of Ralinepag or its pharmaceutically acceptable salts, solvates, or prodrugs without alcoholic beverage.

In further embodiment, the presently disclosed controlled release pharmaceutical composition of ralinepag or its pharmaceutically acceptable salts, solvates, or prodrugs, following oral administration with the alcoholic beverage, provides a mean or median Cmax and/or AUC in a range of about 25% to 200%, such as 50% to 150%, 65% to 150%, 70% to 140%, 80% to 125%, relative to the corresponding pharmacokinetic parameters (mean or median Cmax and/or AUC, respectively) obtained following administration of the same dose of the presently disclosed composition under non-alcoholic conditions.

In a further embodiment, the controlled release pharmaceutical composition of ralinepag or its pharmaceutically acceptable salts, solvates, or prodrugs, when tested in 900 mL of aqueous medium using USP Apparatus II (paddle) at 50 or 150 rpm and 37±1° C., releases less than about 50%, preferably less than about 40%, such as less than 30%, or less than about 25%, of the total drug contained in the composition at 2 hours.

In a further embodiment, the present disclosure provides a method for the treatment of Pulmonary Arterial Hypertension (PAH) with a reduced incidence of side effects, the method comprising administering to a patient in need thereof a therapeutically effective amount of the presently disclosed extended-release pharmaceutical composition of Ralinepag, or a pharmaceutically acceptable salt, solvate, or prodrug thereof, wherein the composition affords protection against alcohol-induced dose dumping when co-administered with an alcoholic beverage. In one embodiment, the presently disclosed pharmaceutical composition of ralinepag or its pharmaceutically acceptable salts, solvates, or prodrugs releases less than about 80% w/w, preferably about 70%, more preferably about 60%, and most preferably about 50%, of the total drug contained in the composition at 2 hours when tested in 900 mL of 40% v/v ethanolic aqueous medium (e.g., 360 mL ethanol and 540 mL of aqueous media, such as any of 0.1 N, 0.01 N, 0.001 N HCl, acetate buffer pH 4.5, or phosphate buffer pH 6.8) using USP Apparatus II (paddle) at 50 (or 75 or 100) rpm and 37±1° C.

In a further embodiment, the extended-release pharmaceutical composition of Ralinepag, or a pharmaceutically acceptable salt, solvate, or prodrug thereof, exhibits a substantially similar in-vitro dissolution profile in both alcoholic and non-alcoholic media, as demonstrated by an $f_2$ similarity factor within the range indicative of equivalence. Specifically, when tested in 900 mL of non-alcoholic aqueous medium and in 40% v/v ethanolic aqueous medium—comprising, for example, 360 mL of ethanol and 540 mL of an aqueous medium such as 0.1 N, 0.01 N, or 0.001 N HCl, acetate buffer at pH 4.5, or phosphate buffer at pH 6.8—the composition provides dissolution profiles meeting similarity criteria ($f_2 \geq 50$) when evaluated using United States Pharmacopeia (USP) Apparatus II (paddle method) operated at 50, 75, or 100 rpm and a temperature of 37±1° C.

In a further embodiment, the presently disclosed extended-release pharmaceutical composition comprising ralinepag or a pharmaceutically acceptable salt, solvate, or prodrug thereof in any maximum tolerable amount, such as any amount from about 0.01 mg to about 5 mg, such as 0.01, 0.02, 0.025, 0.03, 0.04, 0.05, 0.06, 0.07, 0.075, 0.08, 0.09, 0.1, 0.11, 0.12, 0.13, 0.14, 0.15, 0.18, 0.21, 0.24, 0.25, 0.26, 0.28, 0.30, 0.32, 0.36, 0.38, 0.40, 0.42, 0.45, 0.48, 0.50, 0.53, 0.56, 0.60, 0.65, 0.70, 0.75, 0.80, 0.85, 0.90, 0.96, 1.0, 1.1, 1.2, 1.3, 1.4, 1.5, 1.6, 1.8, 2.0, 2.2, 2.4, 2.5, 3.0, 3.5, 4.0, 4.5, or 5.0 mg. However, the preferable amount is withing range of about 0.03 to 3.0 mg, such as 0.03 to 2.0 mg, 0.03 to 1.4 mg, 0.03 to 1.0 mg, 0.03 to 0.8 mg, 0.06 to 2.0 mg, 0.06 to 1.4 mg, 0.06 to 1.0 mg, 0.06 to 0.8 mg, 0.8 to 2.0 mg, 0.08 to 1.4 mg, 0.08 to 1.0 mg, 0.08 to 0.8 mg, 0.1 to 2.0 mg, 0.1 to 1.4 mg, 0.1 to 1.0 mg, 0.1 to 0.8 mg, 0.12 to 2.0 mg, 0.12 to 1.4 mg, 0.12 to 1.0 mg, 0.12 to 0.8 mg, 0.15 to 2.0 mg, 0.15 to 1.4 mg, 0.15 to 1.0 mg, 0.15 to 0.8 mg, 0.18 to 2.0 mg, 0.18 to 1.4 mg, 0.18 to 1.0 mg, 0.18 to 0.8 mg, 0.2 to 2.0 mg, 0.2 to 1.4 mg, 0.2 to 1.0 mg, 0.2 to 0.8 mg, etc.

In preferred embodiment, an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition; and C. at least one of said pharmaceutically acceptable carriers comprises a release rate-controlling ingredient; wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, thereby providing an extended-release profile of ralinepag or a pharmaceutically acceptable salt, solvate, or prodrug thereof, respectively, over a period of about 8 to 24 hours, preferably about 8 to 20 hours, following oral administration.

In preferred embodiment, an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition;

C. at least one of said pharmaceutically acceptable carriers comprises a release rate-controlling ingredient; wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, wherein, the controlled release pharmaceutical composition of ralinepag or its pharmaceutically acceptable salts, solvates, or prodrugs, when tested in 900 mL of aqueous medium containing upto 40% ethanol, using USP Apparatus II (paddle) at 50 or 150 rpm and 37±1° C., releases a. less than about 50%, preferably less than about 40%, such as less than 30%, or less than about 25%, of the total drug contained in the composition at 2 hours, b. more than about 50%, preferably more than about 60%, such as more than 70%, of the total drug contained in the composition at 8 hours, and c. more than about 80%, preferably more than about 85%, of the total drug contained in the composition at 16 hours, thereby providing the extended-release profile of ralinepag or a pharmaceutically acceptable salt, solvate, or prodrug thereof, respectively, over a period of about 8 to 24 hours, preferably about 8 to 20 hours, following oral administration with or without an alcoholic beverage containing up to about 40% alcohol by volume.

In preferred embodiment, an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition;

C. at least one of said pharmaceutically acceptable carriers comprises a release rate-controlling ingredient;

wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, thereby providing an extended-release profile of ralinepag or a pharmaceutically acceptable salt, solvate, or prodrug thereof, wherein the composition:

a. provides controlled release of ralinepag or a pharmaceutically acceptable salt, solvate, or prodrug thereof over an extended period of about 8 to 24 hours following oral administration; and b. following oral administration, with or without an alcoholic beverage containing up to about 40% alcohol by volume, provides 12-hour peak-to-trough plasma concentration ratio of less than about 4, preferably less than about 3.5, and more preferably less than about 2.5.

In preferred embodiment, an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition;

C. at least one of said pharmaceutically acceptable carriers comprises a release rate-controlling ingredient; wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, thereby providing an extended-release profile of ralinepag or a pharmaceutically acceptable salt, solvate, or prodrug thereof, wherein the composition:

a. provides controlled release of ralinepag or a pharmaceutically acceptable salt, solvate, or prodrug thereof over an extended period of about 8 to 24 hours following oral administration; and b. following oral administration, with or without an alcoholic beverage containing up to about 40% alcohol by volume, provides a mean or median Tmax greater than about 2.5 hours, specifically more than 4 hours, and more specifically more than 5 hours, such as more than 6 hours, more than 8 hours.

In preferred embodiment, an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition;

C. at least one of said pharmaceutically acceptable carriers comprises a release rate-controlling ingredient; wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, thereby providing an extended-release profile of ralinepag or a pharmaceutically acceptable salt, solvate, or prodrug thereof, wherein the composition:

a. provides controlled release of ralinepag or a pharmaceutically acceptable salt, solvate, or prodrug thereof over an extended period of about 8 to 24 hours following oral administration; and b. following oral administration, provides a relative mean or median AUC and/or Cmax of the ralinepag or its pharmaceutically acceptable salts, solvates, or prodrugs not more than 150%, such as not more than 145%, not more than 140%, not more than 135%, not more than 130% and not more than 125% relative to the mean or median AUC and/or Cmax of the ralinepag or its pharmaceutically acceptable salts, solvates, or prodrugs, respectively, obtained following the oral administration of the same dose of the controlled release pharmaceutical composition of ralinepag or its pharmaceutically acceptable salts, solvates, or prodrugs with a non-alcoholic beverage.

In preferred embodiment, an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition;

C. at least one of said pharmaceutically acceptable carriers comprises a release rate-controlling ingredient; wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, thereby providing an extended-release profile of ralinepag or a pharmaceutically acceptable salt, solvate, or prodrug thereof, wherein the composition:

a. provides controlled release of ralinepag or a pharmaceutically acceptable salt, solvate, or prodrug thereof over an extended period of about 8 to 24 hours following oral administration; and b. following oral administration, provides a relative mean or median Tmax of the ralinepag or its pharmaceutically acceptable salts, solvates, or prodrugs not more than 150%, such as not more than 145%, not more than 140%, not more than 135%, not more than 130% and not more than 125% relative to the mean or median Tmax of the ralinepag or its pharmaceutically acceptable salts, solvates, or prodrugs, respectively, obtained following the oral administration of the same dose of the controlled release pharmaceutical composition of ralinepag or its pharmaceutically acceptable salts, solvates, or prodrugs with a non-alcoholic beverage.

In preferred embodiment, an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition;

C. at least one of said pharmaceutically acceptable carriers comprises a release rate-controlling ingredient; wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, thereby providing an extended-release profile of ralinepag or a pharmaceutically acceptable salt, solvate, or prodrug thereof, wherein the composition:

a. provides controlled release of ralinepag or a pharmaceutically acceptable salt, solvate, or prodrug thereof over an extended period of about 8 to 24 hours following oral administration; and b. exhibits alcohol resistance such that, when co-administered with an alcoholic beverage containing up to about 40% alcohol by volume, the relative mean or median of any one of $C_{max}$, $T_{max}$, and AUC values of ralinepag or a pharmaceutically acceptable salt, solvate, or prodrug thereof, respectively, remain within about 25% to 200%, preferably 50% to 150%, more preferably 70% to 130% of those obtained under non-alcoholic conditions.

In preferred embodiment, the present disclosure relates to an extended-release pharmaceutical composition comprising ralinepag or a pharmaceutically acceptable salt, solvate, or prodrug thereof, and one or more pharmaceutically acceptable carriers, wherein:

A. the amount of ralinepag or a pharmaceutically acceptable salt, solvate, or prodrug thereof, is from about 0.03 mg to about 3.0 mg, preferably from about 0.3 mg to about 2.0 mg, and most preferably from about 0.3 mg to about 1.4 mg;

B. the one or more pharmaceutically acceptable carriers are present in an amount of not less than 50% w/w of the total weight of the pharmaceutical composition, preferably in an amount of more than 60%, 70%, 75%, 80%, 85%, 90%, or 95% w/w of the total weight of the pharmaceutical composition;

C. at least one of said pharmaceutically acceptable carriers comprises a release rate-controlling ingredient; wherein the release rate-controlling ingredient is present in an amount of either: (i) not less than 25% w/w of the total weight of ralinepag, or the pharmaceutically acceptable salt, solvate, or prodrug thereof, contained in the pharmaceutical composition; or (ii) not less than 2.5% w/w of the total weight of the one or more pharmaceutically acceptable carriers or of the total pharmaceutical composition, such as not less than 3.5%, 5%, 8%, 10%, 15%, 20%, 25%, 30%, 35%, 40%, 50%, or 60% w/w, thereby providing an extended-release profile of ralinepag or a pharmaceutically acceptable salt, solvate, or prodrug thereof, wherein the composition:

a. provides controlled release of ralinepag or a pharmaceutically acceptable salt, solvate, or prodrug thereof over an extended period of about 8 to 24 hours following oral administration; and b. exhibits a substantially similar in-vitro dissolution profile in both alcoholic and non-alcoholic media, as demonstrated by an $f_2$ similarity factor within the range indicative of equivalence ($f_2 \geq$ about 50), when tested in 900 mL of non-alcoholic aqueous medium and in 40% v/v ethanolic aqueous medium using USP Apparatus II (paddle method) at 50 (75, or 100) rpm and a temperature of 37±1° C.

In preferred embodiment, the present disclosure relates to an extended-release oral pharmaceutical composition comprising ralinepag, or a pharmaceutically acceptable salt, solvate, or prodrug thereof, and one or more pharmaceutically acceptable carriers, wherein:

A. the ralinepag, or pharmaceutically acceptable salt, solvate, or prodrug thereof, is present in an amount of about 0.03 mg to about 3.0 mg, preferably about 0.3 mg to about 2.0 mg, and more preferably about 0.3 mg to about 1.4 mg;

B. the one or more pharmaceutically acceptable carriers are present in an amount of not less than 50% w/w of the total weight of the pharmaceutical composition, preferably more than 60%, 70%, 75%, 80%, 85%, 90%, or 95% w/w;

C. at least one of the pharmaceutically acceptable carriers comprises a release-rate-controlling ingredient present in an amount of either (i) not less than 25% w/w of the total weight of ralinepag (or salt, solvate, or prodrug thereof) in the composition, or (ii) not less than 2.5% w/w of the total weight of the one or more carriers or of the total pharmaceutical composition, preferably not less than 3.5%, 5%, 8%, 10%, 15%, 20%, 25%, 30%, 35%, 40%, 50%, or 60% w/w; and D. the composition is alcohol-resistant, such that upon co-administration with an alcoholic beverage containing up to about 40% (v/v) ethanol, the composition:
    i. provides controlled release of ralinepag or a pharmaceutically acceptable salt, solvate, or prodrug thereof over an extended period of about 8 to 24 hours following oral administration;
    ii. exhibits a 12-hour peak-to-trough plasma concentration ratio of less than about 4, preferably less than about 3.5, and more preferably less than about 2.5 (under both alcoholic and non-alcoholic conditions); and
    iii. when tested in 900 mL of 40% v/v ethanolic aqueous medium (USP Apparatus II, 50-100 rpm, 37±1° C.), releases less than 80%, preferably less than 70%, more preferably less than 60%, and most preferably less than 50% of the total ralinepag content at 2 hours.

In preferred embodiment, the present disclosure relates to an extended-release oral pharmaceutical composition comprising ralinepag, or a pharmaceutically acceptable salt, solvate, or prodrug thereof, and one or more pharmaceutically acceptable carriers,
  wherein:
    A. the ralinepag, or pharmaceutically acceptable salt, solvate, or prodrug thereof, is present in an amount of about 0.03 mg to about 3.0 mg, preferably about 0.3 mg to about 2.0 mg, and more preferably about 0.3 mg to about 1.4 mg;
    B. the one or more pharmaceutically acceptable carriers are present in an amount of not less than 50% w/w of the total weight of the pharmaceutical composition, preferably more than 60%, 70%, 75%, 80%, 85%, 90%, or 95% w/w;
    C. at least one of the pharmaceutically acceptable carriers comprises a release-rate-controlling ingredient present in an amount of either (i) not less than 25% w/w of the total weight of ralinepag (or salt, solvate, or prodrug thereof) in the composition, or (ii) not less than 2.5% w/w of the total weight of the one or more carriers or of the total pharmaceutical composition, preferably not less than 3.5%, 5%, 8%, 10%, 15%, 20%, 25%, 30%, 35%, 40%, 50%, or 60% w/w;
    D. the composition provides controlled release of ralinepag or a pharmaceutically acceptable salt, solvate, or prodrug thereof over an extended period of about 8 to 24 hours following oral administration; and
    E. the composition is alcohol-resistant, such that upon co-administration with an alcoholic beverage containing up to about 40% (v/v) ethanol, the composition:
      i. exhibits a 12-hour peak-to-trough plasma concentration ratio of less than about 4, preferably less than about 3.5, and more preferably less than about 2.5 (under both alcoholic and non-alcoholic conditions); and
      ii. when tested in 900 mL of 40% v/v ethanolic aqueous medium (USP Apparatus II, 50-100 rpm, 37±1° C.), releases less than 80%, preferably less than 70%, more preferably less than 60%, and most preferably less than 50% of the total ralinepag content at 2 hours.

In preferred embodiment, the present disclosure relates to a method for the treatment of pulmonary arterial hypertension (PAH), comprising administering the extended-release oral pharmaceutical composition comprising ralinepag or a pharmaceutically acceptable salt, solvate, or prodrug thereof, as disclosed in any of the previous embodiments.

In preferred embodiment, the present disclosure relates to a method for the treatment of pulmonary arterial hypertension (PAH), comprising administering the extended-release oral pharmaceutical composition comprising ralinepag or a pharmaceutically acceptable salt, solvate, or prodrug thereof as disclosed in any of the previous embodiments,
  wherein the administration of said composition provides controlled release of ralinepag or its pharmaceutically acceptable salt, solvate, or prodrug over about 8 to 24 hours, and wherein the composition exhibits alcohol-resistant release properties such that, when co-administered with an alcoholic beverage containing up to about 40% alcohol by volume,
    A. the relative mean or median $C_{max}$, $T_{max}$, and/or AUC values of the drug are within about 25% to 200%, preferably 50% to 150%, and more preferably 70% to 130%, of corresponding values under non-alcoholic conditions; and
    B. the 12-hour peak-to-trough plasma concentration ratio of ralinepag is less than about 4, preferably less than about 3.5, and more preferably less than about 2.5;
    thereby achieving sustained therapeutic plasma concentrations of ralinepag, reducing $C_{max}$-related prostacyclin-associated adverse effects, and maintaining therapeutic efficacy when the composition is administered with or without alcoholic beverages containing up to about 40% alcohol by volume.

The present invention provides extended-release (ER) pharmaceutical compositions of ralinepag or a pharmaceutically acceptable salt, solvate, or prodrug thereof, that provide controlled and sustained release of the active agent over a period of approximately 8 to 24 hours following oral administration. The extended-release formulations described herein are further designed to exhibit robust alcohol resistance, such that their release kinetics, dissolution profile, and pharmacokinetic performance remain substantially unaffected in the presence of alcoholic beverages containing up to about 40% (v/v) ethanol, thereby mitigating the risk of $C_{max}$-related prostacyclin-associated adverse effects when the pharmaceutical composition administered with the alcoholic beverages containing up to about 40% (v/v) ethanol.

For the purpose of detailed discussion and illustration, without limitation, the extended-release compositions of the invention can be classified into five principal categories based on formulation design and release mechanism, namely: (i) matrix systems, (ii) membrane-moderated or reservoir systems, (iii) osmotic delivery systems, (iv) pH-sensitive coated systems, and (v) combination or dual-release systems.

First Class—Matrix-Based Extended-Release Systems

In one embodiment, the extended-release composition is a matrix system in which ralinepag or a pharmaceutically acceptable salt, solvate, or prodrug thereof is dispersed, embedded, or entrapped within a polymeric matrix that controls the rate of drug release through diffusion and/or erosion. The matrix is formulated using alcohol-insoluble or ethanol-stable polymers to ensure consistent performance under both aqueous and hydroalcoholic conditions. The matrix system may be formulated as a single-unit dosage form (e.g., an extended-release tablet or capsules) or as a multiparticulate system comprising microspheres, pellets, or mini-tablets filled into capsules, sachets, or suspended in liquid vehicles.

The matrix polymers may include hydrophilic, hydrophobic, or amphiphilic polymers, or mixtures thereof, selected for their ability to form robust diffusion barriers and maintain mechanical stability in the presence of hydroalcoholic medium. Representative hydrophilic polymers include, but are not limited to: cellulose ethers such as hydroxypropyl methylcellulose (HPMC), hydroxypropyl cellulose (HPC), methylcellulose (MC), carboxymethylcellulose sodium (CMC-Na), and hydroxyethyl cellulose (HEC); polyethylene oxide (PEO) of molecular weight ranging from about 100,000 to 7,000,000 Da; polyvinyl alcohol (PVA); polyvinylpyrrolidone (PVP) and copolymers thereof; natural gums such as xanthan gum, guar gum, gellan gum, acacia, tragacanth, locust bean gum, pullulan, karaya, welan, diutan, and fenugreek gum; polysaccharides including alginates, pectin, pullulan, and chitosan; and polyacrylic acid and derivatives Carbopol® 934P, 971P, 974P, polycarbophil, and cross-linked PAA-PVP copolymers. Representative hydrophobic or water-insoluble polymers include, but not limited to: ethylcellulose; Cellulose esters such as cellulose acetate, cellulose acetate butyrate, and cellulose propionate; polyvinyl acetate, polyvinyl acetate phthalate (PVAP); acrylic and methacrylic polymers, including Eudragit® RS, RL, NE, and NM series (copolymers of acrylic and methacrylic acid esters with quaternary ammonium groups); hydrophobic waxes such as carnauba wax, beeswax, stearic acid, glyceryl monostearate, glyceryl behenate (Compritol® 888 ATO), glyceryl palmitostearate (Precirol® ATO 5), hydrogenated castor oil, cetyl alcohol, stearyl alcohol, hydrogenated vegetable oils, paraffin wax, microcrystalline wax, and cetostearyl alcohol; polyolefins and copolymers such as polyethylene, polypropylene, and ethylene-vinyl acetate (EVA) copolymers; and silicone-based elastomers or polydimethylsiloxane (PDMS) matrices for highly extended release. Representative amphiphilic or swellable polymers includes, but not limited to, Polyethylene oxide-polypropylene oxide block copolymers (Poloxamers) such as Pluronic F68, F127, P105, Polyvinyl acetate-polyvinylpyrrolidone copolymers (e.g., Kollicoat SR 30D), Amidated pectins, hydrophobically modified cellulose ethers, and starch acetate.

In certain embodiment, the matrix polymers comprises combination of a hydrophilic polymer and a hydrophobic polymer (such as ethylcellulose or polymethacrylate) in a ratio of about 20:80 to 95:5, such as 30:70, 40:60, 50:55, and 70:30 to 90:10, to provide a balance of swelling, gel-layer formation, and ethanol-insoluble diffusion control.

Matrix multiparticulates can be prepared by extrusion-spheronization, melt granulation, fluid-bed layering, or solvent evaporation. For instance, a mixture of ralinepag, and at least one of the hydrophilic, hydrophobic, and amphiphilic polymers, optionally with binder and diluent such as cellulose or its derivative such as microcrystalline cellulose, may be first granulated with non-aqueous vehicle, such as alcohol like isopropyl alcohol, aqueous vehicle, or combination thereof, then extruded through a perforated die, spheronized, and dried to yield pellets, which optionally further coated with and at least one of the hydrophilic, hydrophobic, and amphiphilic polymer, to provide extended release and substantially resistance to alcohol-induced dose dumping properties.

Alternatively, melt-granulation may be employed using wax or lipid excipients (such as glyceryl monostearate, cetostearyl alcohol, stearic acid, or hydrogenated vegetable oils). The melt temperature is maintained between 45° C. and 120° C., such as 50-100, 50-90, 55-80° C. to form uniform granules, which upon cooling exhibit granules that provide extended release and substantially resistance to alcohol-induced dose dumping properties.

In a further embodiment, the matrix is prepared via solvent-based granulation using polymers like ethylcellulose, polymethacrylate, or polyvinyl acetate dissolved in non-aqueous solvents (e.g., isopropanol, acetone), optionally with the drug. The granules are dried to remove solvent, producing granules that provide extended release and substantially resistance to alcohol-induced dose dumping properties.

The matrix composition may further include fillers (e.g., any cellulose derivates such as microcrystalline cellulose, lactose, dibasic calcium phosphate, mannitol, sugar or sugar alcohol), glidants (colloidal silica, talc), lubricants (magnesium stearate, stearic acid, sodium stearyl fumarate), plasticizers (e.g., triethyl citrate, diethyl phthalate, triacetin, dibutyl sebacate), and stabilizers (ascorbyl palmitate, tocopherols, BHT).

The optimized matrix formulation provides less than 50% drug release at 2 hours and more than 80% at 16 hours when tested using USP Apparatus II at 50-100 rpm and 37±1° C., with $f_2 \geq 50$ between 0% and 40% ethanol media.

Second Class—Membrane-Moderated (Reservoir) Extended-Release Systems

In another embodiment, the invention provides membrane-controlled or reservoir-type extended-release systems, wherein ralinepag or its pharmaceutically acceptable salt, solvate, or prodrug is contained within a core surrounded by a rate-controlling polymeric membrane. More specifically, a reservoir (inert core) of ralinepag or its pharmaceutically acceptable salt, solvate, or prodrug is surrounded by a rate-limiting membrane (controlled release coating). These individual reservoir system dosage forms may be large, as in the case of a tablet or capsule containing a single large reservoir (inert core), or multiparticulate, as in the case of a plurality of reservoir (inert core) particles, each individually coated with the membrane. The coating can be non-porous, yet permeable to ralinepag or its pharmaceutically acceptable salt, solvate, or prodrug (for example the drug may diffuse directly through the membrane), or it may be porous. As with other embodiments of this invention, the particular mechanism of transport is not believed to be critical, such as drug release occurs primarily by diffusion through, or dissolution-controlled permeation across, the membrane.

Suitable membrane polymers include ethylcellulose, cellulose acetate, cellulose acetate butyrate, polyvinyl acetate, polymethacrylate copolymers (Eudragit RS/RL/NE/NM), polyvinyl alcohol (PVA), and acrylic copolymers. The membrane can optionally include a plasticizer such as triacetin, triethyl citrate, dibutyl sebacate, or polyethylene glycol (PEG 400-6000) to enhance flexibility.

To adjust permeability, the membrane may incorporate pore-forming agents such as sugar, salt, sugar alcohol, hydrophilic polymer (such as cellulose derivative, gum, etc) and/or amphiphilic polymers. These additives, particularly, hydrophilic polymer such as gum, cellulose ether, etc. dissolve gradually in vivo, forming controlled porosity without causing burst release in alcoholic environments. A preferred combination is hydrophobic polymer (such as cellulose ether) in combination with about 5-45%, such as 5-35%, 5-25% of hydrophilic polymer (such as cellulose derivative, gum, etc), sugar, salt, sugar alcohol, and/or amphiphilic polymers to achieve controlled microporous yet ethanol-resistant polymeric film.

Membranes may be applied using aqueous dispersions (e.g., Aquacoat® ECD, Surelease®) or organic or hydroalcoholic coating systems, employing fluid-bed (Wurster), pan, or rotary coaters. Coating thickness is typically adjusted, without any limitation, to yield sustained release of the drug for 8 to 24 hours and further provide an $f_2$ similarity factor ≥50 between 0% and 40% ethanol dissolution profiles. The morphology of the membrane is not of critical importance so long as the permeability characteristics enumerated herein are met.

The membrane can be amorphous or crystalline. It can have any category of morphology produced by any particular process and can be, for example, an interfacially-polymerized membrane (which comprises a thin rate-limiting skin on a porous support), drug permeable membrane, asymmetric membrane, a porous hydrophilic membrane, a porous hydrophobic membrane, a hydrogel membrane, an ionic membrane, and other such materials which are characterized by controlled permeability to the drug. A particularly useful variation of the process for applying a membrane coating comprises dissolving and/or dispersing the coating polymer in a solvent or mixture of solvents chosen such that as the coating dries, a phase inversion takes place in the applied coating solution, resulting in a membrane with a porous structure. Numerous examples of this type of coating system are given in European Patent Specification 0357369 B1, published Mar. 7, 1990, herein incorporated by reference. In general, a support for mechanically strengthening the membrane is not required. For eg., a phase inversion coating may be employed to produce asymmetric membranes. Solvents such as acetone, isopropanol, or ethanol can be used with polymers that undergo controlled phase separation during drying, forming alcohol-insoluble microporous structures.

To adjust mechanical strength, flexibility and/or permeability, the membrane may further incorporate one or more plasticizer and/or glidant. Reservoir core of the drug may further include at least one of the hydrophilic, hydrophobic, and amphiphilic polymers, fillers (e.g., any cellulose derivates such as microcrystalline cellulose, lactose, dibasic calcium phosphate, mannitol, sugar or sugar alcohol), glidants (colloidal silica, talc), lubricants (magnesium stearate, stearic acid, sodium stearyl fumarate), plasticizers (e.g., triethyl citrate, diethyl phthalate, triacetin, dibutyl sebacate), stabilizers (ascorbyl palmitate, tocopherols, BHT), and may include osmotic agents (sorbitol, sodium chloride, potassium chloride, sodium sulfate) to maintain consistent internal pressure for diffusion.

A single larger reservoir such as tablet or capsule can be manufactured by the process known in this art using, in addition of the drug substance, one or more pharmaceutical acceptable material which include, but not limited to, filler, binder, osmotic agents, hydrophilic, swellable or hydrogel polymer, lubricant, glidant, surfactant, and like.

A preferred embodiment of the class of reservoir systems comprises a multiparticulate, wherein each particle is coated with a polymer designed to yield controlled release of the drug. The multiparticulate particles each comprise drug and one or more excipients as needed for fabrication and performance including ion-exchange resin to form drug-ion-exchange resin complex. The size of individual particles is generally between about 50 μm and about 3 mm, although beads of a size outside this range may also be useful.

Reservoir system in the form of multiparticulates may be prepared using techniques known to those skilled in the art, including, but not limited to, the techniques of extrusion and spheronization, wet granulation, fluid bed granulation, rotary bed granulation and forming complexation of drug with ion-exchange resin (drug-ion exchange resin complex). In addition, the beads may also be prepared by building the drug composition (drug plus excipients) up on a seed core (such as a non-pareil seed) by a drug-layering technique such as powder coating or by applying the drug composition by spraying a solution or dispersion of the drug composition in an appropriate binder solution onto seed cores (such as sugar sphere, microcrystalline cellulose sphere, etc) in a fluidized bed such as a Wurster coater or a rotary processor. Another method for manufacturing the multiparticulate cores of this embodiment is the extrusion and spheronization process, as previously discussed for matrix multiparticulates.

A controlled release coating as known in the art, especially polymer coatings, may be employed to fabricate the membrane, as previously discussed, for reservoir systems. Suitable and preferred polymer coating materials, equipment, and coating methods also include those previously discussed.

The rate of the drug release from the coated multiparticulates can also be controlled by factors such as the composition and binder content of the drug-containing core (reservoir), the thickness and permeability of the coating, and the surface-to-volume ratio of the multiparticulates. It will be appreciated by those skilled in the art that increasing the thickness of the coating will decrease the release rate, whereas increasing the permeability of the coating or the surface-to-volume ratio of the multiparticulates will increase the release rate. If desired, the permeability of the coating may be adjusted by blending of two or more materials.

Third Class—Osmotic Delivery Systems

In preferred embodiment, a third class of Ralinepag or its pharmaceutically acceptable salt, solvate, or prodrug extended-release pharmaceutical composition includes the osmotic delivery devices or "osmotic pumps" as they are known in the art. Osmotic pumps comprise a core containing an osmotically effective composition surrounded by a semipermeable membrane. The term "semipermeable" in this context means that water can pass through the membrane, but solutes dissolved in water cannot. In use, when placed in an aqueous environment, the device imbibes water due to the osmotic activity of the core composition. Owing to the semipermeable nature of the surrounding membrane, the contents of the device (including Ralinepag or its pharmaceutically acceptable salt, solvate, or prodrug and any excipients) cannot pass through the non-porous regions of the membrane and are driven by osmotic pressure to leave the device through an opening or passageway pre-manufactured into the dosage form, or alternatively, formed in situ in the gastrointestinal tract by the bursting of intentionally incorporated weak points in the coating under the influence of osmotic pressure.

The osmotically effective composition includes water-soluble osmotic agents that generate a colloidal osmotic pressure, and water-swellable polymers which regulate the release rate of Ralinepag. Examples of osmotic agents include sodium chloride, potassium chloride, mannitol, sorbitol, xylitol, sucrose, glucose, lactose, urea, and citric acid, while suitable swellable polymers include polyethylene oxide (Polyox® grades WSR N80, N750, 303, or 301), hydroxyethyl cellulose, hydroxypropyl methylcellulose (HPMC K4M, K15M, K100M), sodium carboxymethyl cellulose, hydroxypropyl cellulose, crosslinked polyacrylic acid (Carbopol® 934P, 971P), xanthan gum, guar gum, or polyvinyl alcohol. The osmotic core may further contain osmotic modifiers or flux regulators such as polyethylene glycol (PEG 400-6000) or propylene glycol, to adjust water uptake and maintain consistent release under alcoholic and non-alcoholic conditions.

Materials useful for forming the semipermeable membrane include polyamides, polyesters, and cellulose derivatives. Preferred are cellulose ethers and esters. Especially preferred are cellulose acetate, cellulose acetate butyrate, and ethylcellulose. Especially useful materials include those which spontaneously form one or more exit passageways, either during manufacturing or when placed in an environment of use. These preferred materials comprise porous polymers, the pores of which are formed by phase inversion during manufacturing, or by dissolution of a water-soluble component present in the membrane.

The semipermeable membrane may optionally contain plasticizers such as triacetin, triethyl citrate, diethyl phthalate, dibutyl sebacate, acetyl tributyl citrate, castor oil, or polyethylene glycol (PEG 400-6000) in amounts typically ranging from 2% to 20% w/w of the membrane polymer to enhance flexibility and mechanical strength. The membrane may also include pore-forming agents such as sodium chloride, sucrose, mannitol, sorbitol, lactose, hydroxypropyl methylcellulose (HPMC), or polyvinylpyrrolidone (PVP), generally in amounts of about 0.1% to 35, such as 1 to 25% w/w, to modulate permeability. The selected membrane materials substantially maintain membrane integrity and resist alcohol-induced dose dumping when the dosage form is co-administered with alcoholic beverages containing up to about 40% alcohol by volume.

A preferred embodiment of this class of osmotic delivery devices consists of a coated monolayer, bilayer, or trilayer tablet. The coated monolayer tablet comprises a single-layer tablet core containing the Ralinepag or its pharmaceutically acceptable salt, solvate, or prodrug composition and a semipermeable coating surrounding the core tablet that, optionally, contains one or more exit passageways. The coated bilayer tablet comprises (1) a tablet core consisting of two layers: one layer containing the Ralinepag or its pharmaceutically acceptable salt, solvate, or prodrug composition, and another layer consisting of an expandable hydrogel (fluid-expandable polymer), with or without additional osmotic agents; and (2) a semipermeable coating surrounding the core tablet containing one or more exit passageways in communication with the Ralinepag-containing layer for delivering the drug composition.

The coated trilayer tablet comprises (1) a tablet core consisting of three layers: a first layer comprising the Ralinepag or its pharmaceutically acceptable salt, solvate, or prodrug composition, a second layer comprising the Ralinepag or its pharmaceutically acceptable salt, solvate, or prodrug composition, and another layer comprising of an expandable hydrogel (fluid-expandable polymer), with or without additional osmotic agents, wherein the percentage weight of Ralinepag in the second layer with respect to the total weight of the second layer is higher than the percentage weight of Ralinepag in the first layer with respect to the total weight of the first layer; and (2) a semipermeable coating surrounding the core tablet containing one or more exit passageways in communication with the Ralinepag-containing layer for delivering the drug composition, wherein the trilayer coated tablet delivers the Ralinepag or its pharmaceutically acceptable salt, solvate, or prodrug at an ascending rate over an extended period of time, for at least about 4 hours or more.

The layer of Ralinepag or its pharmaceutically acceptable salt, solvate, or prodrug composition comprises, in addition to the active ingredient, one or more pharmaceutically acceptable materials which include, but are not limited to, fillers (microcrystalline cellulose, lactose monohydrate, mannitol, dicalcium phosphate), binders (polyvinylpyrrolidone, hydroxypropyl cellulose, HPMC E5, PVP K30), osmotic agents (sodium chloride, potassium chloride, sorbitol, sucrose, xylitol), osmo-polymers (polyethylene oxide, hydroxyethyl cellulose), hydrophilic or swellable polymers (HPMC K4M, xanthan gum, Carbopol® 974P), lubricants (magnesium stearate, stearic acid, sodium stearyl fumarate), glidants (colloidal silicon dioxide, talc), and surfactants (sodium lauryl sulfate, polysorbate 80, or sorbitan monolaurate).

The rate of Ralinepag or its pharmaceutically acceptable salt, solvate, or prodrug delivery is controlled by such factors as the permeability and thickness of the semipermeable coating, the osmotic activity and water uptake of the hydrogel layer, and the surface area of the dosage form. Those skilled in the art will appreciate that increasing the thickness of the coating will reduce the release rate, whereas increasing the permeability of the coating, osmotic strength of the core, or water activity of the hydrogel layer, or increasing the surface area of the device will enhance the release rate.

Typically, the ratio of osmotic agent to osmo-polymer ranges from about 0.1:1 to 3:0.5 (w/w), and the coating thickness is generally from about 50 μm to 250 μm, depending on the desired release period. By appropriate selection of these parameters, the osmotic delivery devices of Ralinepag provide zero-order extended release for 8 to 24 hours, maintaining a 12-hour peak-to-trough plasma concentration ratio of less than about 4, preferably less than about 3.5, and more preferably less than about 2.5, even when co-administered with alcoholic beverages containing up to about 40% alcohol by volume.

The exit passageway must be located on the side of the tablet containing the Ralinepag or its pharmaceutically acceptable salt, solvate, or prodrug composition. There may be more than one such exit passageway. The exit passageway may be produced by mechanical drilling, laser drilling, or by creating a difficult-to-coat region on the tablet by use of specialized tooling during tablet compression. The diameter of the passageway is typically between 0.2 mm and 1.2 mm, and multiple passageways or passageway with higher diameter may be used to achieve the desired release characteristics. Optionally, the osmotic tablet may be further provided with an outer protective overcoat composed of hydroxypropyl methylcellulose or polyvinyl alcohol to improve mechanical robustness, moisture protection, and alcohol resistance.

The osmotic pump also includes osmotic capsules. The method of manufacturing osmotic capsules as well as osmotic tablets is well known in the art, and is described in detail in many patents issued to Alza Corporation, as well as in "*Osmotic Drug Delivery: A Review of the Patent Literature*," *Journal of Controlled Release* 35 (1995) 1-21, which is incorporated herein by reference.

The osmotic capsule may include a composition containing the Ralinepag or its pharmaceutically acceptable salt, solvate, or prodrug, along with osmotic agents (sodium chloride, mannitol, potassium chloride), osmo-polymers (polyethylene oxide, HPMC, Carbopol), binders (PVP, HPC), fillers (microcrystalline cellulose, lactose, mannitol), and lubricants (magnesium stearate, stearic acid) are filled in capsule shell. The capsules is then coated with a semipermeable membrane made of cellulose acetate, ethylcellulose, cellulose acetate butyrate, or hydroxypropyl methylcellulose acetate succinate (HPMCAS), having one or more preformed or self-generated orifices for controlled release.

Forth Class—Enteric or Delayed Extended Release Composition

In preferred embodiment, a fourth class of Ralinepag or its pharmaceutically acceptable salt, solvate, or prodrug extended-release pharmaceutical composition comprises a pH-sensitive coating surrounding any one of the first, second, or third class extended-release pharmaceutical compositions of Ralinepag or its pharmaceutically acceptable salt, solvate, or prodrug discussed aforesaid. Preferably, the coating comprises a pH-sensitive polymer which is substantially insoluble and/or impermeable at the pH of the stomach, and which becomes more soluble and/or permeable at the pH of the small intestine and/or colon. Preferably, the coating polymer is substantially insoluble and impermeable at pH about <5.0, and water-soluble or permeable at pH>about 5.0.

The pH-sensitive polymers, includes, but not limited to, polyacrylamides, phthalate derivatives such as acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methylcellulose (HPMC) phthalate, methylcellulose phthalate, polyvinyl acetate phthalate (PVAP), polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene-maleic acid copolymers, polyacrylic acid derivatives such as acrylic acid and acrylic ester copolymers, polymethacrylic acid and esters thereof, HPMC acetate succinate, and poly(acrylic-methacrylic acid) copolymers (e.g., Eudragit® L100, L30D-55, S100, FS30D, and L100-55). Other suitable pH-dependent polymers include shellac, zein, ethylcellulose blended with enteric polymer, vinyl acetate-crotonic acid copolymers, and cellulose acetate trimellitate (CAT).

The pH-sensitive coating polymer is typically present in an amount of about 2.5% to 50% w/w of the total weight of the pharmaceutical composition, preferably 3.5% to 35%, such as 4.5 to 25%, 5% to 20%, optionally together with plasticizers as disclosed in the invention but not limited (e.g., dibutyl sebacate, triacetin) and anti-tacking agents (e.g., talc, magnesium stearate, or colloidal silicon dioxide). The coating may be applied as an aqueous dispersion or organic solution using standard coating techniques such as pan coating, fluid-bed coating, or Wurster coating, and provides acid-resistance and site-specific release of Ralinepag in the intestinal region, while maintaining extended-release characteristics under both alcoholic and non-alcoholic conditions.

Fifth Class—Enteric or Delayed Immediate Release Composition

In a preferred embodiment, a fifth class of Ralinepag or its pharmaceutically acceptable salt, solvate, or prodrug extended-release pharmaceutical composition comprises a pH-sensitive coating surrounding a reservoir of Ralinepag or its pharmaceutically acceptable salt, solvate, or prodrug. In this class, a reservoir of Ralinepag or its pharmaceutically acceptable salt, solvate, or prodrug is surrounded by the pH-sensitive coat. These individual reservoir-system dosage forms may be large, as in the case of a tablet or capsule containing a single large reservoir, or multiparticulate, as in the case of a plurality of reservoir particles, each individually coated with the pH-sensitive polymer, using method known in the art or as disclosed previously.

The reservoir core, fabricate to deliver drug in immediate release form, may include, in addition to the active ingredient, one or more pharmaceutically acceptable excipients such as disintegrants such as croscarmellose sodium, sodium starch glycolate, or crospovidone, fillers (such as, but not limited to, microcrystalline cellulose, lactose monohydrate, mannitol, or dicalcium phosphate), optionally matrix-forming polymers (such as, but not limited to, hydroxypropyl methylcellulose, hydroxyethyl cellulose, polyethylene oxide, sodium carboxymethyl cellulose, ethylcellulose, or polyvinylpyrrolidone), binders (such as, but not limited to, HPMC E5, PVP K30, or hydroxypropyl cellulose), lubricants (such as, but not limited to, magnesium stearate, stearic acid, or sodium stearyl fumarate), and surfactants (such as, but not limited to, sodium lauryl sulfate, polysorbate 80).

The pH-sensitive coating may be composed of polymers, optionally with other ingredients, such as those disclosed in the forth class.

Sixth Class—Bi-Phasic or Multiphasic Extended-Release Composition

In a preferred embodiment, the first, second, third, fourth, and fifth classes of Ralinepag or its pharmaceutically acceptable salt, solvate, or prodrug pharmaceutical compositions described herein further comprise an immediate-release dose of Ralinepag or its pharmaceutically acceptable salt, solvate, or prodrug to provide an initial rapid onset of drug action, thereby providing biphasic or multi-phasic in-vivo and in-vitro profile. The immediate-release dose may be incorporated into the pharmaceutical composition in the form of a coating layer surrounding the first, second, third, fourth, and fifth classes of the pharmaceutical composition, as a distinct layer in a multilayer or bilayer tablet, or as granules or beads (pellets) admixed with the first, second, third, fourth, and fifth classes of the pharmaceutical composition within a capsule or sachet.

The immediate-release portion may typically include diluent or filler such as lactose monohydrate, mannitol, or microcrystalline cellulose, one or more disintegrants such as croscarmellose sodium, sodium starch glycolate, or crospovidone, optionally in combination with binders (e.g., PVP K30, HPMC E5), lubricants (e.g., magnesium stearate, sodium stearyl fumarate), and glidants (e.g., colloidal silicon dioxide, talc), depending type of its fabrication.

In this configuration, the bi-phasic or multiphasic pharmaceutical compositions of the ralinepag enables rapid attainment of therapeutic plasma levels of Ralinepag, while the extended-, delayed-extended-, or delayed-release portion maintains sustained plasma exposure over 8 to 24 hours, resulting in controlled pharmacokinetics, reduced $C_{max}$-related prostacyclin adverse effects, and improved patient adherence.

Manufacturing Methods for Various Extended-Release Formulation Designs of Ralinepag and Content Uniformity In a further embodiment, the present invention provides manufacturing methods for preparing various types of the extended-release (ER) pharmaceutical compositions of Ralinepag or its pharmaceutically acceptable salts, solvates, or prodrugs, described herein, which further does not limit the scope of present invention. The manufacturing approach is specifically designed to overcome challenges associated with low-dose drug formulation—notably content uniformity (CU) and segregation—while maintaining alcohol-resistant extended-release performance. Because the active drug loading is extremely low (such as 0.03 mg to 1.4 mg per dosage unit), precise control of blend homogeneity, particle size, and granule distribution is critical to ensuring uniformity from unit to unit, thereby minimizing inter- and intra-subjects pharmacokinetic variability. The present disclosure is directed specifically toward the critical and integrated manufacturing steps required to achieve superior content uniformity (CU) in extended-release pharmaceutical compositions of Ralinepag or its pharmaceutically acceptable salts, solvates, or prodrugs, rather than to general methods of tablet or pellet fabrication that are well known in the art. The disclosed processes address the unique challenges associated with ultra-low-dose drug loading—typically from about 0.03 mg to 1.4 mg per unit—by focusing on process-critical parameters that directly influence CU and segregation control. The presently disclosed methods are applicable to both single-unit dosage forms (such as monolithic or multilayer tablets and capsules) and multi-unit dosage forms (including pellets, beads, mini-tablets, granules, or powder systems). The integrated process design ensures reproducible Ralinepag distribution within and between units, thereby achieving or exceeding USP <905> content-uniformity criteria.

The present disclosure provides specialized process selection that collectively ensure uniform distribution of Ralinepag within the dosage form, prevent segregation due to density or particle size differences, and yield formulations meeting or exceeding USP <905> content uniformity criteria, even under alcohol challenge conditions.

Matrix-Based Extended-Release Formulations

For matrix-type extended-release compositions, Ralinepag or its pharmaceutically acceptable salt, solvate, or prodrug is uniformly dispersed or embedded within a polymeric or lipid matrix that controls drug release through diffusion and/or erosion. Matrix core comprising ralinepag, either in form of single unit core or multiunit cores, it can be manufactured using the following approaches to meet or exceed USP <905> content uniformity criteria.

Manufacturing approaches include:

A. Wet granulation: A preferred process for low-dose APIs, wherein Ralinepag or its pharmaceutically acceptable salt, solvate, or prodrug is either blended directly with excipients or first dissolved in a granulating solution. The drug solution (for example, Ralinepag dissolved in an appropriate organic solvent or dispersed in water, optionally micronized and optionally containing a binder such as polyvinylpyrrolidone K30 (PVP K30) or hydroxypropyl methylcellulose E5 (HPMC E5)) is sprayed onto an excipient powder bed comprising microcrystalline cellulose, lactose monohydrate, or mannitol during the wet-granulation process. The binder promotes agglomeration, and the drying step locks the dissolved or dispersed drug uniformly into the granules. This "solution-spray granulation" approach significantly improves content uniformity for very low-dose drugs compared with conventional powder mixing.

B. Fluid-bed granulation: Powders are suspended in an air stream within a fluid-bed bowl while a Ralinepag-containing binder solution (prepared as disclosed in the wet-granulation approach) is atomized and sprayed onto them. The resulting granules are simultaneously dried, forming uniform, flowable agglomerates. This method distributes the drug at the micron level throughout the powder blend, minimizing segregation and providing reproducible drug loading.

C. High-shear mixing: High-shear or "gentle-wing" mixers can be used to create cohesive granules, improving blend homogeneity for low-dose Ralinepag. Process parameters such as impeller speed, binder addition rate, and mixing time are optimized to achieve consistent granulation and to ensure low relative standard deviation in assay values across batches.

D. Melt granulation: Ralinepag is combined with a low-melting wax or lipid such as glyceryl behenate (Compritol® 888 ATO), glyceryl monostearate, stearic acid, or cetostearyl alcohol. Heating forms a homogeneous melt, which is then cooled, milled or sieved, and compressed. This process avoids solvents and provides matrix integrity as well as resistance to alcohol-induced dose dumping.

E. Dry granulation (roller compaction): In one embodiment, dry granulation, also referred to as roller compaction or slugging, is employed when Ralinepag or its pharmaceutically acceptable salt, solvate, or prodrug is sensitive to moisture or elevated temperature. This process eliminates the need for liquid binders and solvents. In a preferred approach, Ralinepag is first mixed and blended with a small portion of one or more excipients to form a pre-blend ensuring uniform distribution of the low-dose drug. The pre-blend is then sequentially combined with additional portions of excipients—for example, microcrystalline cellulose, lactose monohydrate, mannitol, or dicalcium phosphate—using a geometric dilution technique until all excipients are uniformly mixed with the drug. The resulting homogeneous powder blend is then subjected to roller compaction or slugging/deslugging, where the powder is compressed into ribbons or slugs and subsequently milled to form granules of controlled particle size. The granules are then sieved and lubricated prior to compression into tablets or encapsulation. This method enhances flow properties, bulk density, and content uniformity while avoiding the exposure of Ralinepag to heat or moisture, making it especially suitable for low-dose extended-release formulations.

Direct Compression and Low-Dose Blending Techniques

In a further embodiment, the present invention provides an extended-release matrix core comprising Ralinepag or its pharmaceutically acceptable salt, solvate, or prodrug, prepared by a direct compression process, configured either as a single-unit core (such as a tablet) or as multi-unit cores (such as pellets, minitablets, or granules encapsulated within a capsule). In certain embodiments, a direct compression approach may be utilized to prepare low (5-10% w/w), medium (11-25% w/w) or ultra-high-dose (>25% w/w) extended-release pharmaceutical compositions of Ralinepag or its pharmaceutically acceptable salts, solvates, or prodrugs. Although direct compression is conventionally regarded as unsuitable for very low-dose or ultra-low dose (such as <5% w/w, such as <4%, <3%, <2%, <1%) formulations due to blending and segregation challenges, this method provide uniform drug distribution and content uniformity even at doses below about 1.4 mg per unit when executed under specific process and material parameters. Accordingly, the present invention provides an inventive direct-compression platform that yields pharmaceutically acceptable content uniformity in low-dose within USP <905> content uniformity criteria, yet reproducible, alcohol-resistant, extended-release dosage forms.

Direct compression offers a simple yet critical manufacturing route for low-dose Ralinepag extended-release formulations. Achieving CU under such low loading requires specialized blending, dilution, and segregation control techniques. The method therefore represents an inventive and non-obvious adaptation of direct compression technology for ultra-low-dose, extended-release formulations. The direct compression process comprises a one or combination of multiple interdependent operations, as described below, each contributing to the improved uniformity and robustness of the final blend.

A. Geometric dilution: Ralinepag initially mixes with an equal portion of one or more diluents, such as microcrystalline cellulose or lactose monohydrate, to form a pre-blend. The pre-blend then be combined sequentially with equal portions of additional diluents or other excipient until the full excipient mass is incorporated. This stepwise geometric dilution technique facilitate gradual and uniform distribution of Ralinepag throughout the blend, thereby minimizing the risk of localized concentration gradients even at sub-milligram loading.

B. Carrier excipients: The process employ directly compressible carrier excipients with irregular or porous surface morphology, such as Avicel® PH 102, ProSolv SMCC, Ludiflash®, directly compressible similar carrier or diluent. These carriers may adsorb and immobilize fine Ralinepag particles, enhancing blend homogeneity and reducing segregation during handling, blending, and compression. The use of such engineered excipients particularly advantageous in maintaining micron-level uniformity for low-dose formulations.

C. Continuous blending: In some embodiments, a continuous direct-compression system may be employed to ensure consistent mixing and real-time control of blend uniformity. The Ralinepag and excipients may be continuously metered via loss-in-weight feeders and fed into a continuous mixer, which may maintain dynamic homogenization of the blend. This continuous process may mitigate the segregation and variability typically encountered in batch mixing and may yield reproducible CU across extended production runs.

D. Geometric shifting and blending: In certain embodiments, Ralinepag or its pharmaceutically acceptable salt, solvate, or prodrug initially sifted with an equal portion of one or more diluents, such as microcrystalline cellulose or lactose monohydrate, to form a pre-blend. The pre-blend may then be combined sequentially with equal portions of additional diluents or other excipients, with each portion being sifted and optionally blended prior to addition of the next portion, until the full excipient mass has been incorporated and sifted. Perform final blending after final sift and necessary lubrication blending. This stepwise geometric sifting and blending technique may facilitate gradual and uniform distribution of Ralinepag throughout the blend, thereby minimizing the risk of localized concentration gradients even at sub-milligram loading.

E. Dry blending and sifting: In certain embodiments, Ralinepag or its pharmaceutically acceptable salt, solvate, or prodrug and one or more excipients are initially pre-blended, then optionally sifted with an equal portion of one or more diluents, such as microcrystalline cellulose or lactose monohydrate, to form a pre-blend. Following blending, sifting or screening and then final blending, and optionally lubrication blending, is conducted to achieve uniform granule size and flowability before compression.

The coordinated applications of multiple interdependent operations as described above, while preparing single-unit core (such as a tablet) or as multi-unit cores (such as pellets, minitablets, or granules encapsulated within a capsule) provides a surprising improvement in content uniformity for Ralinepag formulations at ultra-low dosage levels, yields consistent unit-to-unit dosage, uniform dissolution profiles, and reliable pharmacokinetic parameters with lower variation. The direct compression process described herein therefore provides a robust, scalable, and reproducible approach for the manufacture of low-dose, alcohol-resistant, extended-release Ralinepag dosage forms.

Reservoir and Membrane-Coated Systems

In further embodiments, the present invention provides reservoir-type extended-release pharmaceutical compositions of Ralinepag or its pharmaceutically acceptable salts, solvates, or prodrugs, configured either as single-unit systems (for example, tablet or capsules) or as multi-unit systems (for example, pellets, beads, mini-tablets, or granules). In such compositions, the active ingredient may be incorporated within a coated core, wherein Ralinepag is contained either within the core matrix itself—in the case of single-unit or multi-unit systems or as a drug layer deposited around an inert core, such as a placebo core (manually for single- or multi-unit), sugar sphere, microcrystalline cellulose seed, or other pharmaceutically inert substrate.

For single-unit or multi-unit compositions wherein the drug resides within the core, granules may be prepared according to the granulation and blending methods described in Section A or B. In such cases, the controlled-release excipient may be partially or entirely replaced by pharmaceutically acceptable diluents or fillers, or employed in combination with one or more diluents or fillers to optimize compression characteristics, flowability, and blend uniformity. Suitable diluents or fillers may include microcrystalline cellulose, lactose monohydrate, mannitol, dibasic calcium phosphate, starch, or isomalt.

For multi-unit core compositions, the resulting granules may be extruded and spheronized or compressed into mini-cores. For single-unit or multi-unit compositions wherein the drug is incorporated in the coating layer, a Ralinepag solution or dispersion (for example, Ralinepag dissolved in an appropriate organic solvent or dispersed in purified water, optionally micronized and optionally containing a binder such as polyvinylpyrrolidone K30 (PVP K30) or hydroxypropyl methylcellulose E5 (HPMC E5)) may be sprayed onto inert cores (such as placebo cores, sugar spheres, or microcrystalline cellulose seeds) using a fluid-bed coating system (for example, a Wurster process), using powder layer technique, or by drug-layering in a pan coater.

The resulting drug-containing core, prepared by either methods, is subsequently coated on its outer surface with a controlled- and/or delayed-release polymeric membrane designed to regulate the rate of Ralinepag release over an extended period of time. These reservoir-type systems provide precise control of Ralinepag release, while maintaining content uniformity (CU) even at ultra-low dose levels (e.g., 0.3-1.4 mg per unit).

Osmotic-Controlled Systems

In further embodiments, the present invention provides osmotic-controlled extended-release pharmaceutical compositions of Ralinepag or its pharmaceutically acceptable salts, solvates, or prodrugs, developed to provide controlled, reproducible drug release, substentially independent of gastrointestinal pH or motility, while ensuring content uniformity (CU) in low-dose formulations meeting USP <905> criteria.

This embodiment addresses a critical formulation challenge associated with ultra-low-dose osmotic systems, wherein conventional processes often fail to achieve uniform drug distribution and consistent osmotic performance. The presently disclosed approach integrates low-dose granulation and blending strategies with optimized osmotic polymer composition and membrane engineering to achieve uniformity, controlled hydration, and release stability, even at Ralinepag doses as low as 0.3-1.4 mg per unit.

The osmotic system typically comprises a core—configured as a single-, bi-, or tri-layer tablet—that contains Ralinepag and osmotically active excipients, enclosed within a semipermeable membrane. The membrane allows controlled water ingress but limits solute egress, enabling osmotic pressure-driven release through a precisely engineered orifice.

In certain embodiments, Ralinepag is incorporated within the core matrix, wherein granules are prepared according to the granulation and blending methods described in Section A or B. The granules include osmotic agents (e.g., sodium chloride, potassium chloride, mannitol, or sorbitol), osmopolymers (e.g., HPMC, hydroxyethyl cellulose, polyethylene oxide), binders (e.g., PVP K30), and fillers (e.g., microcrystalline cellulose, lactose, or dibasic calcium phosphate). The resulting granules exhibit improved flowability and uniform drug distribution and may be compressed into mono-, bi-, or tri-layer tablets.

The semipermeable coating may comprise cellulose acetate, ethyl cellulose, cellulose acetate butyrate, or related cellulose esters, optionally containing plasticizers such as triacetin, triethyl citrate, or PEG 4000 to adjust permeability and mechanical integrity. One or more delivery orifices (typically 0.25-0.6 mm in diameter) may be formed by laser drilling or mechanical perforation to regulate release of the drug solution generated within the hydrated core.

In bilayer or trilayer embodiments, the top (pull) layer may include the Ralinepag formulation, while the bottom (push) layer comprises swellable, hydrophilic polymers, optionally with osmotic agent, that generate osmotic pressure. The trilayer configuration may further incorporate gradient loading of Ralinepag in the middle (second pull) layer, providing a controlled, ascending-rate release over at least 8 hours.

The integration of low-dose blending uniformity, osmotic polymer optimization, and alcohol-resistant semipermeable coating design results in a robust extended-release system that maintains release stability in hydroalcoholic conditions (up to 40% v/v ethanol). This ensures consistent pharmacokinetic performance, minimized $C_{max}$-related adverse effects, and improved patient tolerability.

Particle Size of Ralinepag

In certain embodiments, the presently disclosed extended-release pharmaceutical composition comprises Ralinepag, or a pharmaceutically acceptable salt, solvate, or prodrug thereof, having an average particle size ($D_{90}$) of, in the final composition, not greater than about 150 μm, for example about 125 μm, about 100 μm, about 80 μm, about 50 μm, about 25 μm, about 20 μm, or about 10 μm. Without being bound by theory, controlling the particle-size distribution of Ralinepag within this range—more specifically, between about 0.1 μm and about 50 μm—is believed to facilitate homogeneous dispersion of the active ingredient in ultra-low-dose formulations (e.g., less than about 1.4 mg per unit dose), even when the drug is incorporated in solid particulate form and not completely dissolved during any of the manufacturing processes described herein. Such particle-size control minimize segregation and enhance blend uniformity, and thereby enable the robust manufacture of low dose extended-release compositions in which the drug remains substantially in non-solution form, such as a solid state, solid dispersion, or partially soluble state (not more than about 50%, such as 40%, 30%, 25%, 20%, 15%, 10% of total Ralinepag, thereby preventing drug recrystallization and maintaining particle-size integrity), during the manufacturing process. As ralinepag is water insoluble, the drug recrystallization and particle size morphology critically impact in-vitro and in-vivo performance of the pharmaceutical composition.

In certain embodiments, the fine particle-size distribution of Ralinepag contributes to improved content uniformity (CU) of the final dosage form, suitable to meet or exceed USP <905> acceptance criteria (AV≤15), while maintaining the desired extended-release and alcohol-resistant characteristics of the composition. This approach provides a solvent-free and scalable formulation strategy particularly suitable for ultra-low-dose extended-release Ralinepag systems, where maintaining content uniformity and release robustness presents a significant manufacturing challenge.

This particle-size-based formulation design provides a technically distinctive approach compared with conventional solvent-based granulation or solution-spray processes typically used to achieve low-dose uniformity. By enabling solvent-free, scalable, and reproducible manufacture, the invention addresses the long-standing challenge of content-uniformity control in ultra-low-dose, alcohol-resistant extended-release systems of Ralinepag and its pharmaceutically acceptable derivatives.

The integrated process design of the present invention ensures that each individual dosage unit, whether configured as a single-unit system (for example, a monolithic or multilayer tablet or capsule) or as a multi-unit system (for example, pellets, beads, granules, or mini-tablets), achieves and maintains content uniformity (CU) meeting or exceeding the requirements of USP <905>. The extended-release pharmaceutical compositions of Ralinepag or its pharmaceutically acceptable salts, solvates, or prodrugs thereby obtained exhibit reproducible pharmacokinetic performance, and substantially reduced inter- and intra-subject variability, collectively ensuring therapeutic reliability and dosage reproducibility over prolonged administration. Accordingly, the present invention establishes a novel and inventive process platform in which method selection and process parameter optimization-rather than routine formulation design alone-serve as the critical determinants of content uniformity and extended-release reproducibility in low-dose Ralinepag compositions. The inventive methods disclosed herein provide robust, scalable, and reproducible industrial applicability across diverse dosage architectures, thereby addressing an unmet need in the development of low-dose, alcohol-resistant, extended-release Ralinepag formulations.

In further embodiments, the present invention provides that the extended-release pharmaceutical compositions of Ralinepag, or its pharmaceutically acceptable salts, solvates, or prodrugs, may be fabricated in two or more dosage strengths to enable individualized administration according to patient-specific therapeutic requirements. It has been surprisingly observed, however, that fabricating multiple strengths by simple weight-proportional scaling, that is, by proportionally increasing or decreasing the total formulation weight in direct relation to the active drug content—can lead to significant alterations in alcohol-induced release behavior. Such proportional scaling changes the total volume and geometry of the final dosage form and thereby disrupts the matrix porosity, diffusion path length, and surface-area-to-volume ratio, which collectively contribute to the extended-release and alcohol-resistant performance of the formulation. This phenomenon results in unpredictable release kinetics and may cause dose dumping under hydroalcoholic conditions.

Accordingly, the present invention provides a controlled-scaling approach for fabricating multi-strength extended-release Ralinepag compositions, particularly using same formulation platform to attain proportional pharmacokinetic (particularly for AUC and/or Cmax within 65 to 150%, such as 70 to 140%, preferably 80 to 125% between strengths), wherein the total tablet or unit weight between any two strengths does not deviate by more than about 50%, such as not more than (NMT) about 40%, 30%, 25%, 20%, 15%, or 10% relative to each other. Furthermore, the relative difference in the absolute amount (in milligrams) of one or more controlled-release polymers between strengths is maintained within about 50%, such as NMT 40%, 30%, 25%, 20%, 15%, or 10%, to ensure compositional consistency across strengths.

Such proportionality control ensures that the matrix density, and surface-area-to-volume relationship remain substantially constant among all dosage strengths, as determined by a dissolution similarity factor $(f_2) \geq 50$ between the strengths, thereby preserving the alcohol-resistant release characteristics and ensuring comparable dissolution kinetics under both aqueous and hydroalcoholic conditions (for example, up to 40% v/v ethanol). The resulting multi-strength Ralinepag compositions thus provide dose flexibility without compromising extended-release performance, content uniformity, or patient safety.

In the present invention, the terms "material," "excipient," "ingredient," and "component" are used interchangeably. One skilled in the art will recognize that these terms are open-ended and may encompass multiple functional roles within a single pharmaceutical composition.

According to the present invention, the term controlled-release materials encompass water-insoluble materials, hydrophilic polymers or materials, swellable polymers, hydrogel polymers, water-soluble polymers, and pH-sensitive polymers, individually or in combination. The terms "controlled-release material," "release rate controlling ingredient," and "release retardant" are interchangeable and refer to any material capable of controlling, sustaining, or retarding the release of Ralinepag or its pharmaceutically acceptable salts, solvates, or prodrugs from the dosage form.

The pharmaceutical composition may contain controlled-release material(s) in an amount from about 0.01% w/w to about 99.9% w/w, such as about 0.5% w/w to about 95% w/w, about 1% w/w to about 85% w/w, about 1.5% w/w to about 75% w/w, about 2.5% w/w to about 65% w/w, about 5% w/w to about 55% w/w, about 5% w/w to about 35% w/w, of the total composition weight.

The term "water-insoluble material" or "hydrophobic material" refers to any component substantially insoluble in water but capable of modulating permeability or forming a diffusion barrier. Suitable examples include, but not limited to: Cellulose-based polymers-Cellulose acetate, cellulose acetate butyrate, cellulose acetate propionate, cellulose tri-acetate, cellulose nitrate, ethyl cellulose, microcrystalline cellulose, cellulose acetate phthalate, cellulose acetate trimellitate, cellulose acetate succinate, cellulose propionate, and cellulose ethers. Hydrophobic lipids and waxes-microcrystalline wax, beeswax, paraffin wax, hydrogenated vegetable oils, hydrogenated cottonseed oil, hydrogenated palm oil, castor wax, carnauba wax, stearyl alcohol, cetyl alcohol, stearic acid, glyceryl monostearate, glyceryl behenate (Compritol® 888 ATO), glyceryl palmitostearate, glyceryl distearate, glyceryl tristearate, cetostearyl alcohol, acetylated monoglycerides, glyceryl monooleate, or partial esters of glycerin. Synthetic hydrophobic polymers-Polymethyl methacrylate (PMMA), polymethacrylate copolymers (e.g., Eudragit® RL 100, RS 100, NE 30D), NM 30D)), polyvinyl acetate, ethylene-vinyl acetate copolymer, polycaprolactone, poly(lactic acid), poly(lactic-co-glycolic acid), polycarbonate, polydimethylsiloxane, and polyurethane dispersions. Fatty substances and derivatives-hydrogenated castor oil, myristyl alcohol, cetyl palmitate, stearyl stearate, palmitic acid, oleic acid, lauric acid, stearoyl macrogolglycerides, cetyl palmitate, acetylated monoglycerides, glyceryl distearate, glyceryl monooleate, isopropyl myristate, isopropyl palmitate, PEG stearates, and wax-alcohol blends, or mixtures thereof. In one embodiment, the dosage form comprises water-insoluble materials in an amount of 0.1%-80% w/w, preferably 5%-60% w/w, and most preferably 10%-40% w/w of the total weight of the composition.

Suitable hydrophilic, swellable, hydrogel, and water-soluble polymers include natural, semi-synthetic, or synthetic ingredients such as, but not limited to: Cellulose ethers: hydroxypropyl methylcellulose (HPMC; grades K4M, K15M, K100M), hydroxyethyl cellulose (HEC), hydroxypropyl cellulose (HPC), methylcellulose (MC), carboxymethyl cellulose (CMC), and sodium carboxymethyl cellulose (NaCMC). Polysaccharides and gums: xanthan gum, guar gum, gellan gum, locust bean gum, pullulan, tragacanth, acacia gum, carrageenan, alginic acid and sodium alginate, pectin, konjac glucomannan, or chitosan. Polyalkylene oxides: polyethylene oxide (PEO; molecular weight 100 k-7,000 k), polypropylene oxide, copolymers of ethylene oxide and propylene oxide, or poloxamers (e.g., Pluronic®). Acrylic and methacrylic polymers: Carbomers (Carbopol® 934, 940, 974P, 980NF), polyacrylic acid, polymethacrylates, methacrylic acid copolymers (Eudragit® L100, S100, RL, RS, NE), and crosslinked polyacrylic acid derivatives. Natural gums and polysaccharides: Xanthan gum, guar gum, gellan gum, locust bean gum, pullulan, acacia, tragacanth, carrageenan, fenugreek gum, konjac glucomannan, welan gum, and sodium alginate. Polyvinyl polymers: polyvinylpyrrolidone (PVP K12-K90), copovidone (PVP/VA), polyvinyl alcohol (PVA), and polyvinyl caprolactam. Proteins and polypeptides: gelatin, casein, soy protein, albumin, polylysine. Starches: native or modified starch, pregelatinized starch, amylose, amylopectin, dextrin, maltodextrin, and cyclodextrin derivatives. Synthetic hydrophilic polymers: Polyvinylpyrrolidone (PVP K12-K90), copovidone (PVP/VA 64), polyvinyl alcohol (PVA), polyethylene glycol (PEG 4000-35000), polyvinyl caprolactam, poly(2-oxazoline) s, polyvinyl acetate phthalate, and PEG-PLA copolymers. The hydrophilic or hydrogel polymer component is typically present in an amount from about 0.1% w/w to 90% w/w, such as 2%-70% w/w, 3.5%-50% w/w of the total weight of the composition.

The term "hydrophilic material" refers to substances soluble in water and includes salts (e.g., sodium chloride, potassium chloride), sugars (e.g., mannitol, sucrose), acids and bases (e.g., citric acid, sodium bicarbonate), and polymers described above. Such hydrophilic materials may be incorporated in amounts from about 0.1% w/w to about 80% w/w, such as 1%-50% w/w, 1.5%-35% w/w of the formulation, depending on the desired dissolution and release characteristics.

The pharmaceutical compositions of the invention may further include one or more pharmaceutically acceptable additives, selected according to their function. Examples and typical concentration ranges are described below.

Fillers or diluents may be used to increase bulk and improve blend uniformity. Suitable examples include: microcrystalline cellulose (Avicel® PH 101, 102, 301, 302), silicified microcrystalline cellulose (ProSolv® SMCC), lactose monohydrate, anhydrous lactose, mannitol, sorbitol, maltitol, isomalt, xylitol, trehalose, dicalcium phosphate dihydrate, tribasic calcium phosphate, calcium sulfate, magnesium carbonate, starch, pregelatinized starch, compressible sugar, and spray-dried mannitol. Fillers or diluents are typically present in amounts from about 1% to 95% w/w, preferably about 10%-70% w/w, more preferably about 15%-60% w/w of the total composition.

Suitable disintegrants include crospovidone (Polyplasdone®), croscarmellose sodium (Ac-Di-Sol®), sodium starch glycolate (Explotab®), pregelatinized starch, starch, low-substituted hydroxypropyl cellulose (L-HPC), and ion-exchange resins. Disintegrants may be present at 0.1%-25% w/w, preferably 0.5%-15% w/w, most preferably 1%-10% w/w.

Anti-tacking agents and lubricant include stearates (e.g., magnesium stearate, calcium stearate, zinc stearate), talc, fumed silica, glyceryl monostearate, polyethylene glycol (PEG 4000-6000), sodium lauryl sulfate, and waxes. They may be incorporated in concentrations of 0.01%-10% w/w, such as 0.1%-5% w/w, 0.5%-2%, to prevent agglomeration during coating or blending.

Binders serve to impart cohesiveness to powders during granulation and may include HPMC (E3-E15), HPC, PVP (K12-K90), copovidone, maltodextrin, acacia, sodium alginate, starch paste, gelatin, or polyethylene glycol. Binders may be used at 0.1%-25% w/w, preferably 1%-10% w/w, depending on the granulation method employed.

Plasticizers enhance film flexibility and include: triacetin, triethyl citrate, acetyl triethyl citrate, acetyl tributyl citrate, dibutyl sebacate, PEG 200-8000, propylene glycol, glycerin, diethyl phthalate, tributyl citrate, sorbitol, and polysorbate esters. Plasticizers are generally present at about 0.1%-50% w/w, preferably about 0.5%-25% w/w, about 1%-20% w/w relative to polymer weight.

Stabilizers such as antioxidants are incorporated to prevent oxidative degradation of Ralinepag. Examples include ascorbic acid, sodium metabisulfite, butylated hydroxyanisole (BHA), butylated hydroxytoluene (BHT), tocopherols, and citric acid. Typical use levels are 0.01%-2% w/w, preferably 0.05%-1% w/w.

Natural and synthetic sweeteners include mannitol, sorbitol, sucrose, dextrose, fructose, aspartame, acesulfame potassium, sucralose, neotame, and cyclamate. Sweeteners are typically used at 0.1%-10% w/w, depending on the desired taste masking.

Preferred coloring agents include iron oxides (red, yellow, black), titanium dioxide, caramel, and FD&C or D&C lakes or dyes. Coloring agents are typically used at 0.001%-5% w/w, preferably 0.01%-2% w/w.

Sugars suitable for use include sucrose, glucose, lactose, maltose, fructose, trehalose, mannitol, xylitol, sorbitol, and isomalt. Sugars may be incorporated as fillers, sweeteners, or osmotic agents at 1%-70% w/w, preferably 5%-50% w/w.

Water-soluble salts include sodium chloride, potassium chloride, magnesium sulfate, calcium chloride, and phosphate salts such as sodium dihydrogen phosphate or disodium hydrogen phosphate. Typically used at 0.1%-20% w/w, preferably 0.5%-10% w/w.

Osmotic agents include sugars (e.g., sucrose, dextrose, mannitol) and salts (e.g., sodium chloride, potassium chloride, magnesium sulfate, sodium sulfate). They may be included at 0.5%-70% w/w, preferably 5%-40% w/w, depending on osmotic driving requirements.

Suitable surfactants include polysorbates (20, 40, 60, 80), sorbitan esters, sodium lauryl sulfate, dioctyl sodium sulfosuccinate, polyoxyethylene stearate, cetyl alcohol ethoxylates, PEG 40 castor oil, poloxamers (Pluronic®), and lecithin. Surfactants may be present at 0.01%-10% w/w, preferably 0.05%-5% w/w, depending on drug wettability and solubility characteristics.

The functional classification and typical concentration ranges of pharmaceutically acceptable excipients described herein are consistent with those provided in the *Handbook of Pharmaceutical Excipients,* 6th Edition, edited by Raymond C. Rowe, Paul J. Sheskey, and Marian E. Quinn, which is incorporated herein by reference in its entirety. The excipients and materials listed above are presented for illustrative purposes only and are not intended to limit the scope of the invention. Any pharmaceutically acceptable excipient, material, or combination that performs the equivalent function and supports the extended-release, low-dose, and alcohol-resistant characteristics of the Ralinepag pharmaceutical composition shall be deemed within the scope of the present disclosure.

The selection, proportion, and physicochemical characteristics of the excipients described herein—including particle size distribution, surface morphology, compressibility, and hydrophilic-hydrophobic balance—are integral to the manufacturing methods of the present invention. These excipient systems, when employed in conjunction with the disclosed low-dose granulation and direct-compression processes, enable uniform dispersion of Ralinepag or its pharmaceutically acceptable salts, solvates, or prodrugs throughout the dosage matrix or multi-unit core. Such rational excipient selection minimizes segregation, enhances powder flow and compressibility, and maintains blend homogeneity even at sub-milligram API loadings, thereby achieving or exceeding USP <905> content uniformity criteria. The synergistic interaction between excipient functionality and the critical manufacturing parameters described herein constitutes a key inventive aspect of the present disclosure, ensuring reproducible extended-release performance and alcohol resistance across single-unit and multi-unit dosage forms.

It will be appreciated that the present invention is not limited to the particular methods of fabricating controlled-release dosage forms of Ralinepag or its pharmaceutically acceptable salts, solvates, or prodrugs as specifically described herein. In other words, a person of ordinary skill in art, having the benefit of the present disclosure, will recognize that controlled-release pharmaceutical compositions of Ralinepag may likewise be prepared using alternative manufacturing techniques or process variations without departing from the spirit or scope of the invention.

EXAMPLES

Example 1—Extended-Release Matrix Tablets of Ralinepag (Wet Granulation Method)

Formulation Composition:

| Component | Function | % w/w |
|---|---|---|
| Ralinepag | Active ingredient | 0.2 |
| Microcrystalline cellulose | Filler/Matrix | 40.0 |
| Lactose monohydrate | Filler | 14.7 |

-continued

| Component | Function | % w/w |
|---|---|---|
| Hydroxypropyl methylcellulose (HPMC) | Release-retardant | 30.0 |
| Xanthan Gum | Release-retardant | 11.0 |
| Polyvinylpyrrolidone K30 | Binder | 3.0 |
| Colloidal silicon dioxide | Glidant | 0.5 |
| Magnesium stearate | Lubricant | 1.0 |
| Total | | 100.0 |

Manufacturing Procedure:

Sieving and Preparation of Raw Materials: Pass all solid excipients through a #40 mesh sieve to achieve uniform particle size. Collect the sieved materials in labeled stainless-steel containers.

Pre-Blending: Transfer Ralinepag, microcrystalline cellulose, and lactose monohydrate into a blender. Blend for 10 minutes at 15 rpm to achieve uniform distribution of the low-dose API.

Binder Solution Preparation: Dissolve PVP K30 (3% w/w) in purified water under continuous stirring at ambient temperature until a clear solution forms.

Wet Granulation: Transfer the pre-blend to a high-shear mixer granulator. Start impeller at 100 rpm and chopper at 1,000 rpm, and gradually add the binder solution over 3-5 minutes. Continue mixing until a cohesive wet mass forms.

Screening and Drying: Pass the wet mass through a #16 mesh screen to form uniform granules. Dry the granules in a tray dryer or fluid bed dryer (FBD) at 45° C. until the desired LOD is obtained.

Sizing: Pass the dried granules through a #20 mesh to break aggregates and ensure uniform particle size.

Final Blending: Transfer the granules to a blender and add HPMC, xanthan gum, and colloidal silicon dioxide. Blend for 10 minutes to ensure homogeneity.

Lubrication: Add magnesium stearate (sieved #60 mesh) and blend for 5 minutes at low speed.

Compression: Compress the final blend on a rotary press to achieve tablets of approximately 200 mg weight.

The resulting tablets provide controlled release of Ralinepag over 8 hours, maintaining content uniformity (CU) within USP <905> limits.

Example 2—Extended-Release Matrix Tablets by Dry Granulation (Roller Compaction)

Formulation Composition:

| Component | Function | % w/w |
|---|---|---|
| Ralinepag | Active ingredient | 0.5 |
| Microcrystalline cellulose (Avicel ® PH102) | Filler/Matrix | 55.0 |
| Lactose monohydrate | Filler | 8.5 |
| Polyethylene Oxide | Matrix polymer | 35.0 |
| Colloidal silicon dioxide | Glidant | 0.2 |
| Magnesium stearate | Lubricant | 0.8 |
| Total | | 100.0 |

Manufacturing Procedure:

Sieving: Pass all excipients through a #40 mesh sieve.

Pre-Blending: Mix Ralinepag with a portion (one-tenth) of microcrystalline cellulose and lactose in a double-cone blender for 10 minutes to form a pre-blend.

Geometric Dilution: Sequentially add equal portions of remaining excipients using geometric dilution and continue blending until all powders are uniformly mixed.

Roller Compaction: Transfer the final blend into a roller compactor. Perform the roller compaction and collect compacted ribbons.

Milling and Sieving: Mill ribbons using a granulator fitted with a 1 mm screen. Pass through a #20 mesh sieve to achieve uniform granule size.

Blending and Lubrication: Add colloidal silicon dioxide and magnesium stearate to the granules and blend gently for 5 minutes.

Compression: Compress granules into 200 mg tablets.

The process minimizes segregation and provides excellent flow and content uniformity meet USP <905>, suitable for ultra-low-dose extended-release formulations.

Example 3—Fluid-Bed Coated Pellets (Reservoir System)

Formulation Composition:

| Component | Function | % w/w |
|---|---|---|
| Ralinepag | Active ingredient | 0.7 |
| PVP K30 | Binder (drug-layering) | 2.6 |
| Sugar spheres | Inert core | 74.45 |
| Ethylcellulose (Aquacoat ECD 30) | Rate-controlling polyme | 15 |
| Guar Gum | Pore former | 2.5 |
| Talc | Anti-tacking agent | 1 |
| Dibutyl Sebacate | Plasticizer | 3.75 |
| Total | | 100.0 |

Manufacturing Procedure:

Drug-Layering Suspension: Add Ralinepag and PVP K30 in a water-ethanol (40:60) mixture under stirring until clear. Pass through a #100 mesh filter.

Drug Layering: Load sugar spheres into a fluid-bed coater (Wurster process). Set initial inlet air temperature at 50° C., atomizing air pressure at 1.0 bar, and spray rate at 2-5 g/min. Spray the drug solution until target drug load is achieved. Adjust parameter as required.

Drying: Dry pellets at 45° C. for 30 minutes to remove residual solvent.

Coating Step: Prepare a coating dispersion of Aquacoat ECD 30, guar gum, dibutyl sebacate and talc. Apply it to drug-loaded pellets using the same fluid-bed coater until target weight gain is achieved.

Curing: Cure coated pellets at 45-50° C. to stabilize the film.

Encapsulation: Fill 200 mg pellets equivalent to 1.4 mg drug-loaded pellets into size 0 gelatin capsules.

The coated pellets show uniform drug release and alcohol resistance up to 40% v/v ethanol.

Example 5—Osmotic-Controlled Extended-Release Tablets

Formulation Composition:

| Layer/Component | Function | % w/w Ex. 5A 0.6 mg | % w/w Ex. 5B 1.2 mg |
|---|---|---|---|
| Drug Layer | | | |
| Ralinepag | Active ingredient | 0.6 | 1.2 |
| Mannitol | Osmotic agent | 19.4 | 19.4 |
| Sodium chloride | Osmotic agent | 10 | 10 |
| Hydroxyethyl Cellulose | Matrix/Osmo polymer | 14 | 14 |

-continued

| | | % w/w | |
| --- | --- | --- | --- |
| Layer/Component | Function | Ex. 5A 0.6 mg | Ex. 5B 1.2 mg |
| Polyethylene oxide (low viscosity) | Osmopolymer | 30 | 30 |
| Lactose monohydrate | Filler | 23 | 22.4 |
| PVP K30 | Binder | 2 | 2 |
| Magnesium stearate | Lubricant | 1.0 | 1.0 |
| Push Layer | | | |
| Polyethylene oxide (high viscosity) | Swellable polymer | 70.0 | 70.0 |
| Sodium chloride | Osmotic agent | 38.5 | 38.5 |
| Magnesium stearate | Lubricant | 1.0 | 1.0 |
| Ferric oxide (optional) | Colorant | 0.5 | 0.5 |
| Coating | | | |
| Cellulose acetate | Semipermeable membrane | 94 | 94 |
| Polyethylene Glycol 3350 | Plasticizer | 6 | 6 |
| Total | | 100.0 | 100.0 |

Manufacturing Procedure:

Granulation: Blend drug layer components, add PVP K30 solution (5% w/w in water), and wet-granulate in a high-shear mixer. Dry at 45° C. until target LOD is attained. Sift the dried granules through appropriate screen, mill oversize granules and then sift milled granules through screen.

Push Layer Preparation: Dry blend polyethylene oxide, sodium chloride, lubricant, colorant, and magnesium stearate in a planetary mixer for 10 minutes.

Compression: Compress Bilayer Tablets as Follow:

| Strength | Example | Formulation Strategy | Preparation of Bi-layer tablet Core |
| --- | --- | --- | --- |
| 0.6 mg 1.2 mg | 5A 5B | Nominal Ratios Held Constant by % w/w between strength (substantially same amount of total weight of formulation and controlled release ingredients) | Compress bilayer tablets with the 100 mg drug layer first followed by the 100 mg push layer using a bilayer tablet press, making total weight of 200 mg bi-layer tablet. |
| 0.6 mg | 5C | Proportional by Drug Load Concentration | Compress bilayer tablets using granules of example 5B by proportionally decreasing amount of formulation composition (using 50% amount of granules of example 5B): the 50 mg drug layer first followed by the 50 mg push layer using a bilayer tablet press to formulate Ralinepag 0.6 mg Tablets, making total weight of 100 mg bi-layer tablet |

Coating: Coat tablets of examples 5A, 5B, and 5C with cellulose acetate in acetone: water containing Polyethylene Glycol 3350 until weight gain of 15 or 20% is achieved. Dry coated tablets at 45° C.

Orifice Drilling: Drill a 0.5 mm laser orifice on the drug-layer side.

Tablets of example 5A and 5B substantially provide similar dissolution provide while tablets of example 5C provide substantially faster release compared to examples 5A and 5B.

Example 6—Direct Compression Tablets Via Geometric Sifting and Blending Vs without Geometric Dilution or Sifting Formulation Composition:

| | | % w/w | |
| --- | --- | --- | --- |
| Component | Function | Example 6A Geometric Sifting and Blending | Example 6B Without Geometric Dilution or Sifting |
| Ralinepag | Active ingredient | 0.25 | 0.25 |
| Mannitol | Filler | 28.25 | 28.25 |
| Microcrystalline cellulose (MCC) (Avicel PH102) | Filler/Matrix | 25 | 25 |
| Xanthan Gum | Matrix polymer | 30 | 30 |
| Polyethylene oxide | Release modifier | 15 | 15 |
| Colloidal silicon dioxide | Glidant | 0.5 | 0.5 |
| Magnesium stearate | Lubricant | 1 | 1 |
| Total | | 100.0 | 100.0 |

Manufacturing Procedure:

Sifting: Sift all ingredients through a #30 mesh screen before blending.

Example 6A Only: Stepwise Geometric Blending: Mix Ralinepag with an equal portion of mannitol and microcrystalline cellulose to form a pre-blend and sift it through #40 mesh screen. Sequentially add equal portions of remaining excipients (xanthan gum, PEO, MCC) with intermediate sifting through a #30 mesh, continue until all material are mixed and sifted. Continue stepwise blending for 10 minutes per addition.

Blending:

A. Example 6A: Transfer the full blend of step 2 to a blender and mix for 10 minutes at 16 rpm.

B. Example 6B: Transfer the sifted material of step 1 to a blender and mix for 10 minutes at 16 rpm.

Lubrication: Add colloidal silicon dioxide and magnesium stearate (pre-sieved #60 mesh). Blend for 5 minutes at low speed.

Compression: Compress the final blend of step 4, for example 6A and 6B separately as independent operation, into tablets of 100 mg average weight using appropriate punches to prepare Ralinepag tablet of 0.25 mg strength.

Even though Examples 6A and 6B employ the same overall formulation composition, Example 6A provide superior blend homogeneity and content uniformity, even at an active loading of less than 1% w/w of Ralinepag, as compared to Example 6B.

What is claimed is:

1. An extended-release pharmaceutical composition comprising ralinepag or a pharmaceutically acceptable salt, solvate, or prodrug thereof, and one or more pharmaceutically acceptable carriers, wherein:

a. the amount of the ralinepag or pharmaceutically acceptable salt, solvate, or prodrug thereof contained in the composition is from about 0.03 mg to about 1.2 mg, and the ralinepag has an average particle size ($D_{90}$) within about 0.1 μm to 50 μm to facilitate homogeneous dispersion for ultra-low-dose formulations of the ralinepag or pharmaceutically acceptable salt, solvate, or prodrug thereof;

b. the one or more pharmaceutically acceptable carriers are present in an amount of not less than 85% w/w of the total weight of the pharmaceutical composition; and c. at least one of the one or more pharmaceutically acceptable carriers comprises one or more release rate-controlling ingredients, wherein the one or more release rate-controlling ingredients is present in an amount not less than about 5% w/w of the total weight of the one or more pharmaceutically acceptable carriers or of the total pharmaceutical composition, and wherein the composition:

a. provides controlled release of the ralinepag or a pharmaceutically acceptable salt, solvate, or prodrug thereof over an extended period of about 8 to 24 hours following oral administration;

b. when administered orally to a human subject, including with an alcoholic beverage containing up to 40% (v/v) alcohol, provides a 12-hour peak-to-trough plasma concentration ratio of less than about 4.0, and a $T_{max}$ greater than about 4 hours;

c. releases less than about 40% of the ralinepag or pharmaceutically acceptable salt, solvate, or prodrug thereof at 2 hours when tested in 900 mL of aqueous medium using USP Apparatus II at 50 rpm and 37±1° C.;

d. releases less than about 50% of the ralinepag or pharmaceutically acceptable salt, solvate, or prodrug thereof at 2 hours, more than about 60% at 8 hours, and more than about 80% at 16 hours when tested in 900 mL of aqueous medium containing up to 40% ethanol using USP Apparatus II at 50 rpm and 37±1° C.;

e. consists of the ralinepag or a pharmaceutically acceptable salt, solvate, or prodrug thereof as sole active ingredient; and f. provides substantially bioequivalent pharmacokinetic profiles within ±about 25% $C_{max}$ and/or AUC, when administered under alcoholic and non-alcoholic conditions, respectively.

2. The composition of claim 1, wherein the ralinepag or pharmaceutically acceptable salt, solvate, or prodrug thereof is substantially in a non-solution state, selected from a solid state, solid dispersion, or partially soluble form, during manufacturing of the composition.

3. The composition of claim 1, wherein the pharmaceutical composition is manufactured by a process comprising one or more critical steps selected from:

a. dissolving the ralinepag or its pharmaceutically acceptable salt, solvate, or prodrug to form a solution or dispersion for use in wet granulation, fluid-bed granulation, or coating of an inert core; or b. employing the ralinepag or a pharmaceutically acceptable salt, solvate, or prodrug thereof in a substantially non-solution state, selected from a solid state, solid dispersion, or partially soluble form, when manufactured by a process comprising one or more operations selected from dispersing or dissolving the drug in a melted excipient during melt granulation, geometric dilution techniques including geometric mixing, geometric sifting, geometric blending, or combinations thereof, and sequential addition of excipients under controlled shear to ensure uniform distribution and reproducible content uniformity across dosage units.

4. The composition of claim 1, wherein the composition is fabricated in two or more dosage strengths to enable individualized administration according to patient-specific therapeutic requirements, wherein the extended-release and alcohol-resistant characteristics are substantially retained across multiple dosage strengths of the same formulation platform as determined by a dissolution similarity factor ($f_2$) ≥50 between the strengths.

5. The composition of claim 4, wherein the total unit weight of one strength to another does not deviate by more than about 35%.

6. The composition of claim 4, wherein the absolute weight of one or more release-rate-controlling ingredients between the strengths is within about 35%.

7. The composition of claim 4, wherein dissolution profiles of any two dosage strengths, when tested using USP Apparatus II at 50 rpm in 900 mL of aqueous medium, exhibit an $f_2$ similarity factor of at least 50 under both aqueous and hydroalcoholic (40% v/v ethanol) conditions.

8. The composition of claim 1, wherein one or more release rate-controlling ingredients is selected from the group consisting of hydroxypropyl methylcellulose, hydroxypropyl cellulose, hydroxyethyl cellulose, sodium carboxymethylcellulose, hydroxyethyl methylcellulose, ethylcellulose, cellulose acetate, cellulose acetate butyrate, cellulose acetate phthalate, cellulose triacetate, polyvinyl alcohol, polyvinyl acetate, polyethylene oxide, polyvinylpyrrolidone, copovidone, poly(meth)acrylates including eudragit RS, RL, NE, L, S, and E, polymethacrylic acid copolymers, polyacrylic acid derivatives, carbomer, polycarbophil, polyethylene glycol, poly(ethylene-vinyl acetate) copolymer, polycaprolactone, poly(lactic-co-glycolic acid), xanthan gum, guar gum, locust bean gum, carrageenan, alginic acid and its salts, chitosan, pectin, gelatin, carnauba wax, beeswax, stearic acid, glyceryl monostearate, glyceryl behenate, glyceryl palmitostearate, hydrogenated castor oil, cetyl alcohol, stearyl alcohol, hydrogenated vegetable oils, paraffin wax, microcrystalline wax, and cetostearyl alcohol, pH-dependent polymers, and mixtures thereof.

9. The composition of claim 8, wherein one or more pH-dependent polymers is selected from the group consisting of polyacrylamides, acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methylcellulose (HPMC) phthalate, methylcellulose phthalate, polyvinyl acetate phthalate (PVAP), polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene-maleic acid copolymers, acrylic acid and acrylic ester copolymers, polymethacrylic acid and esters thereof, HPMC acetate succinate, and poly(acrylic-methacrylic acid) copolymers.

10. The composition of claim 1 is formulated as a tablet, capsule, multiparticulate pellet, or osmotic pump system suitable for once-daily oral administration.

11. The composition of claim 1 is suitable for once-daily oral administration to a mammal in need thereof for the treatment of pulmonary arterial hypertension, or other diseases responsive to IP-receptor agonism, providing stable plasma exposure and reduced $C_{max}$-related side effects.

12. The composition of claim 1, wherein the one or more pharmaceutically acceptable carriers comprises at least one or more release rate-controlling ingredients, at least one filler or diluent, and optionally one or more binders, glidants, lubricants, or disintegrants, collectively present in an amount of not less than 85% w/w of the total weight of the pharmaceutical composition.

13. The composition of claim 1 is formulated as a matrix system, in which the ralinepag or pharmaceutically acceptable salt, solvate, or prodrug thereof is dispersed, embedded, or entrapped within a polymeric matrix of one or release more rate-controlling ingredients that controls the rate of drug release through diffusion and/or erosion.

14. The composition of claim 1 is formulated as a reservoir system, wherein the ralinepag or its pharmaceutically acceptable salt, solvate, or prodrug is contained within a core surrounded by a coat comprising one or release more rate-controlling ingredients.

15. The composition of claim 1 is formulated as an osmotic system, wherein the ralinepag or its pharmaceutically acceptable salt, solvate, or prodrug is contained within an osmotically effective core composition surrounded by a semipermeable membrane coat that comprises one or more release rate-controlling ingredients.

16. The composition of claim 1 further comprises a pH-sensitive coat surrounding it, wherein the pH-sensitive coat comprises one or more pH-sensitive polymers selected from the group consisting of polyacrylamides, acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methylcellulose (HPMC) phthalate, methylcellulose phthalate, polyvinyl acetate phthalate (PVAP), polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene-maleic acid copolymers, acrylic acid and acrylic ester copolymers, polymethacrylic acid and esters thereof, HPMC acetate succinate, and poly(acrylic-methacrylic acid) copolymers.

17. The composition of claim 1 is formulated as a delayed immediate-release composition, wherein the ralinepag or its pharmaceutically acceptable salt, solvate, or prodrug thereof is contained within an immediate-release core surrounded by the pH-sensitive coat comprising one or more pH-dependent polymers selected from the group consisting of polyacrylamides, acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methylcellulose (HPMC) phthalate, methylcellulose phthalate, polyvinyl acetate phthalate (PVAP), polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene-maleic acid copolymers, acrylic acid and acrylic ester copolymers, polymethacrylic acid and esters thereof, HPMC acetate succinate, and poly(acrylic-methacrylic acid) copolymers.

18. The composition of claim 1 provides a content uniformity acceptance value (AV) of not greater than 15%, when determined per USP <905>.

* * * * *